United States Patent [19]

Ueno

[11] Patent Number: 5,346,921
[45] Date of Patent: Sep. 13, 1994

[54] TREATMENT OF INFLAMMATION WITH 15-KETO-PROSTAGLANDIN COMPOUNDS

[75] Inventor: Ryuji Ueno, Hyogo, Japan

[73] Assignee: R-Tech Ueno, Ltd., Osaka, Japan

[21] Appl. No.: 972,092

[22] Filed: Nov. 5, 1992

Related U.S. Application Data

[63] Continuation of Ser. No. 726,672, Jul. 8, 1991, abandoned.

[30] Foreign Application Priority Data

Jul. 10, 1990 [JP] Japan .................... 2-184963

[51] Int. Cl.$^5$ .................. A61K 31/19; A61K 31/557; A61K 31/12
[52] U.S. Cl. ..................... 514/573; 514/690
[58] Field of Search ................. 514/573, 690

[56] References Cited

U.S. PATENT DOCUMENTS

| 4,072,755 | 2/1978 | Buendia et al. | 424/312 |
|---|---|---|---|
| 4,097,603 | 6/1978 | Robert | 424/305 |
| 4,452,794 | 6/1984 | Kort et al. | 424/240 |
| 4,612,330 | 9/1986 | Mynderse et al. | 514/557 |

FOREIGN PATENT DOCUMENTS

| 153858 | 9/1985 | European Pat. Off. . |
|---|---|---|
| 0153858 | 9/1985 | European Pat. Off. . |
| 0268388 | 5/1988 | European Pat. Off. . |
| 281239 | 9/1988 | European Pat. Off. . |
| 284180 | 9/1988 | European Pat. Off. . |
| 0284180 | 9/1988 | European Pat. Off. . |
| 289349 | 11/1988 | European Pat. Off. . |
| 292177 | 11/1988 | European Pat. Off. . |
| 308135 | 3/1989 | European Pat. Off. . |
| 310305 | 4/1989 | European Pat. Off. . |
| 330511 | 8/1989 | European Pat. Off. . |
| 342003 | 11/1989 | European Pat. Off. . |
| 343904 | 11/1989 | European Pat. Off. . |
| 345951 | 12/1989 | European Pat. Off. . |
| 2217602 | 11/1989 | United Kingdom . |

OTHER PUBLICATIONS

"The Biological Activities of Three Metabolites of Prostaglandin $E_1$", by E. Anggard, Acta Physiologica Scandinavica, (1966), pp. 66, 509–510.

Robert Berkow et al, "The Merck Manual of Diagnosis and Therapy", 15th Edition, (1987), pp. 2511–2512, Merck & Co., Inc., Rahway, N.J., U.S.A.

Primary Examiner—Marianne M. Cintins
Assistant Examiner—Kimberly R. Jordan
Attorney, Agent, or Firm—Sughrue, Mion, Zinn, Macpeak & Seas

[57] ABSTRACT

A method of treatment of inflammatory diseases which comprises administering, to a subject in need of such treatment, an anti-inflammatorily effective amount of a 15-keto-prostaglandin compound.

12 Claims, No Drawings

TREATMENT OF INFLAMMATION WITH 15-KETO-PROSTAGLANDIN COMPOUNDS

This is a continuation of application Ser. No. 07/726,672 filed Jul. 8, 1991, now abandoned.

BACKGROUND OF THE INVENTION

1. Field of the Invention

The present invention relates to a treatment of inflammatory diseases with a 15-ketoprostaglandin compound.

Prostaglandins (hereinafter, prostaglandins are referred to as PGs) are members of a class of organic carboxylic acid that are contained in human and most other mammalian tissues or organs and that exhibit a wide range of physiological activities. Naturally occurring PGs possess as a common structural feature the prostanoic acid skeleton:

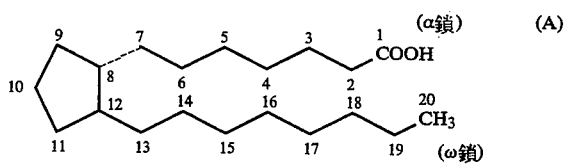

Some synthetic analogues have somewhat modified skeletons. The primary PGs are classified based on the structural feature of the five-membered cycle moiety into PGAs, PGBs, PGCs, PGDs, PGEs, PGFs, PGGs, PGHs, PGIs and PGJs, and also on the presence or absence of unsaturation and oxidation in the chain moiety as:

Subscript 1—13,14-unsaturated-15-OH
Subscript 2—5,6- and 13,14-diunsaturated-15-OH
Subscript 3—5,6- 13,14- and 17,18-triunsaturated-15-OH Further, PGFs are sub-classified according to the configuration of hydroxy group at 9 into α(hydroxy group being in the alpha configuration) and β(hydroxy group being in the beta configuration).

2. Background Information

PGE$_1$, PGE$_2$ and PGE$_3$ are known to have vasodilating, hypotensive, gastro-juice reducing, intestine-hyperkinetic, uterine contracting, diuretic, bronchodilating and anti-ulcer activities. Also, PGF$_{1\alpha}$, PGF$_{2\alpha}$ and PGF$_{3\alpha}$ are known to have hypertensive, vasocontracting, intestine-hyperkinetic, uterine contracting, luteoregressive and bronchocontracting activities.

In addition, some 15-keto (i.e. having an oxo group at position 15 in place of the hydroxy group) prostaglandins and 13,14-dihydro-15-ketoprostaglandins are known as substances naturally produced by enzymatic actions during metabolism of primary PGs (Acta Physiologica Scandinavica, 66., 509, 1966). It has also been described that 15-ketoprostaglandin F$_{2\alpha}$ has an anti-pregnant activity.

European Patent Application No. 0,310,305 describes that 15-keto-PGs can be used as catharitics. However, it has not been reported that 15-ketoprostaglandin compounds are therapeutically effective in the treatment of inflammatory diseases.

As a result of extensive studies about the biological properties of 15-ketoprostaglandin compounds, the present inventors have discovered that these compounds are useful as an agent for treating inflammatory diseases.

SUMMARY OF THE INVENTION

In a first aspect, the present invention provides a method for treatment of inflammatory diseases which comprises administering, to a subject in need of such treatment, an anti-inflammatorily effective amount of a 15-ketoprostaglandin compound.

In a second aspect, the present invention provides a use of a 15-ketoprostaglandin compound for the manufacture of a medicament for treatment of inflammatory diseases.

In a third aspect, the present invention provides a pharmaceutical composition for treatment of inflammatory diseases comprising a 15-ketoprostaglandin compound in association with a pharmaceutically acceptable carrier, diluent or excipient.

DETAILED DESCRIPTION OF THE INVENTION

The term "inflammatory disease" means lesions caused by a defensive reaction or an inflammatory reaction of a living body against harmful influence of circumstances (such as physical, chemical and biological circumstances) having signs of redness, heat, pain, swelling and loss of function.

The term "anti-inflammatory" means a tendency or an ability to act against or protect from or inhibit the inflammatory reaction. The 15-keto-prostaglandin compounds used in the instant invention have such tendency or ability.

As used herein, the term "treatment" or "treating" refers to any means of control of a disease in a mammal, including preventing the disease, curing the disease, relieving the disease and arresting or relieving the development of the disease.

The term "15-ketoprostaglandin compounds", referred to as 15-keto-PG compounds, include any prostaglandin derivatives which have an oxo group in place of the hydroxy group at position 15 of the prostanoic acid nucleus irrespective of the presence or absence of the double bond between positions 13 and 14.

Nomenclature

Nomenclature of 15-keto-PG compounds herein uses the numbering system of prostanoic acid represented in formula (A) shown above.

While formula (A) shows a basic skeleton having twenty carbon atoms, the 15-keto-PG compounds used in the present invention are not limited to those having the same number of carbon atoms. The carbon atoms in Formula (A) are numbered 2 to 7 on the α-chain starting from the α-carbon atom adjacent to the carboxylic carbon atom which is numbered 1 and towards the five-membered ring, 8 to 12 on the said ring starting from the carbon atom on which the α-chain is attached, and 13 to 20 on the ω-chain starting from the carbon atom adjacent to the ring. When the number of carbon atoms is decreased in the α-chain, the number is deleted in order starting from position 2 and when the number of carbon atoms is increased in the α-chain, compounds are named as substituted derivatives having respective substituents at position 1 in place of carboxy group (C-1). Similarly, when the number of carbon atoms is decreased in the ω-chain, the number is deleted in order starting from position 20 and when the number of carbon atoms is increased in the ω-chain, compounds are named as substituted derivatives having respective substituents at position 20. Stereochemistry of the compounds is the same as that of above formula (A) unless otherwise specified. Thus, 15-keto-PG compounds having 10 carbon atoms in the ω-chain is nominated as 15-keto-20-ethyl-PGs.

The above formula expresses a specific configuration which is the most typical one, and in this specification compounds having such a configuration are expressed without any specific reference to it.

In general, PGDs, PGEs and PGFs have a hydroxy group on the carbon atom at position 9 and/or 11 but in the present specification the term "15-keto-PG compounds" includes PGs having a group other than a hydroxyl group at position 9 and/or 11. Such PGs are referred to as 9-dehydroxy-9-substituted-PG compounds or 11-dehydroxy-11-substituted-PG compounds.

As stated above, nomenclature of 15-keto-PG compounds is based upon the prostanoic acid. These compounds, however, can also be named according to the IUPAC naming system. For example, 13,14-dihydro-15-keto16R,S-fluoro-PGE$_2$ is (Z)-7-{(1R,2R,3R)-3-hydroxy-2-[(4R,S)-4-fluoro-3-oxo-1-octyl]-5-oxocyclopentyl}hept-5-enic acid. 13,14-dihydro-15-keto-20-ethyl-11-dehydroxy-11R-methyl-PGE$_2$ methyl ester is methyl 7-{(1R,2S,3S)-3-methyl-2-[3-oxo-1-decyl]-5-oxo-cyclopentyl}-hept-5-enoate. 13,14-dihydro-6,15-diketo-19-methyl-PGE$_2$ ethyl ester is ethyl 7-{(1R,2S,3S)-3-hydroxy-2-(7-methyl-3-oxo-1-octyl)-5-oxo-cyclopentyl}-6-oxo-heptanoate. 13,14-dihydro-15-keto-20-ethyl-PGF$_{2\alpha}$ isopropyl ester is isopropyl (Z)-7-[(1R,2R,3R,5S)-3,5-dihydroxy-2-(3-oxo-1-decyl)-cyclopentyl]-hept-5-enoate. 13,14-dihydro-15-keto-20-methyl-PGF$_{2\alpha}$ methyl ester is methyl (Z)-7-[(1R,2R,3R,5S)-3,5- dihydroxy-2-{3-oxo-1-nonyl}-cyclopentyl]-hept-5-enonate.

Preferred Compounds

The 15-keto-PG compounds used in the present invention may be any derivatives of PG insofar as they have an oxo group at position 15 in place of the hydroxy group, and may have a double bond between positions 13 and 14 (15-keto-PG subscript 1 compounds), two double bonds between positions 13 and 14 as well as positions 5 and 6 (15-keto-PG subscript 2 compounds), or three double bonds between positions 13 and 14, positions 5 and 6 as well as positions 17 and 18 (15-keto-PG subscript 3 compounds), and may have a single bond between positions 13 and 14 (13,14-dihydro-15-keto-PG compounds).

Typical examples of the compounds used in the present invention are 15-keto-PG subscript 1, 15-keto-PG subscript 2, 15-keto-PG subscript 3, 13,14-dihydro-15-keto-PG subscript 1, 13,14-dihydro-15-keto-PG subscript 2, and 13,14-dihydro-15-keto-PG subscript 3, wherein PG is as defined above as well as their derivatives.

Examples of substitution products or derivatives include esters at the carboxy group at the alpha chain, pharmaceutically or physiologically acceptable salts, unsaturated derivatives having a double bond or a triple bond between positions 2 and 3 or positions 5 and 6, respectively, substituted derivatives having substituent(s) on carbon atom(s) at position 3, 5, 6, 16, 17, 19 and/or 20 and compounds having lower alkyl or a hydroxy (lower) alkyl group at position 9 and/or 11 in place of the hydroxy group, of the above PGs.

Examples of substituents present in preferred compounds are as follows: Substituents on the carbon atom at position 3, 17 and/or 19 include lower alkyl, for example, $C_{1-4}$ alkyl, especially methyl and ethyl. Substituents on the carbon atom at position 16 include lower alkyl e.g. methyl, ethyl etc., hydroxy and halogen atom e.g. chlorine, fluorine, aryloxy e.g. trifluoromethylphenoxy, etc. Substituents on the carbon atom at position 17 include halogen atom e.g. chlorine, fluorine, etc. Substituents on the carbon atom at position 20 include saturated and unsaturated lower alkyl e.g. $C_{1-4}$ alkyl, lower alkoxy e.g. $C_{1-4}$ alkoxy and lower alkoxy (lower) alkyl e.g. $C_{1-4}$ alkoxy-$C_{1-4}$ alkyl. Substituents on the carbon atom at position 5 include halogen atom e.g. chlorine, fluorine, etc. Substituents on the carbon atom at position 6 include oxo group forming carbonyl. Stereochemistry of PGs having hydroxy, lower alkyl or lower (hydroxy) alkyl substituent on the carbon atom at position 9 and/or 11 may be alpha, beta or mixtures thereof.

Said derivatives may have an alkoxy, phenoxy or phenyl group at the end of the omega chain where the chain is shorter than the primary PGs.

Especially preferred compounds are those having a lower alkyl e.g. methyl, ethyl etc., a halogen atom e.g. chloro, fluoro etc. at position 16, those having a halogen atom e.g. chloro, fluoro etc. at position 17, those having a lower alkyl e.g. methyl, ethyl etc. at position 19, those having a halogen atom e.g. chloro, fluoro etc. at position 5, those having an oxo group at position 6, those having a lower alkyl, e.g. methyl, ethyl, etc. at position 20 and those having phenyl or phenoxy which are optionally substituted with halogen or haloalkyl at position 16 in place of the rest of the alkyl chain.

A group of preferred compounds used in the present invention has the formula

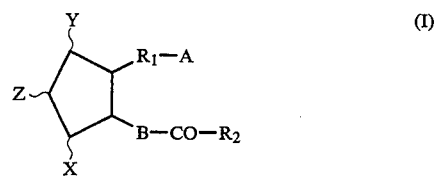
(I)

wherein X and Y are hydrogen, hydroxy, halo, lower alkyl, hydroxy(lower)alkyl, or oxo, with the proviso that at least one of X and Y is a group other than hydrogen, and 5-membered ring may have at least one double bond, Z is hydrogen or halo, A is —CH$_2$OH, —COCH$_2$OH, —COOH or its functional derivative, B is —CH$_2$—CH$_2$, —CH=CH— or —C≡C—, R$_1$ is bivalent saturated or unsaturated, lower or medium aliphatic hydrocarbon residue which is unsubstituted or substituted with halo, oxo or aryl, R$_2$ is saturated or unsaturated, lower or medium aliphatic hydrocarbon residue which is unsubstituted or substituted with halo, hydroxy, oxo, lower alkoxy, lower alkanoyloxy, cyclo(lower)alkyl, aryl or aryloxy.

Among the compounds of the above formula, the compounds represented by the following formula are novel.

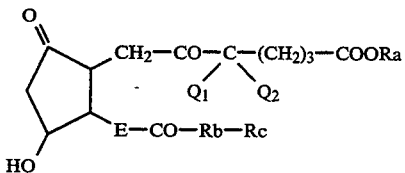

(II)

wherein $Q_1$ is halogen, $Q_2$ is hydrogen or halogen, E is $-CH_2-CH_2-$ or $-CH=CH-$, Ra is hydrogen or lower alkyl, Rb is single bond or lower alkylene, and Rc is lower alkyl which is unsubstituted or substituted with halogen, lower cycloalkyl which is unsubstituted or substituted with lower alkyl, monocyclic aryl which is unsubstituted or substituted with halogen or halo(-lower) alkyl, or monocyclic aryloxy which is unsubstituted or substituted with halogen or halo(lower) alkyl or a pharmaceutically acceptable salts in case of Ra is hydrogen.

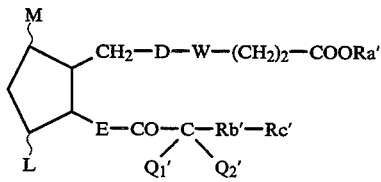

(III)

wherein

L and M are hydrogen atom, hydroxy, lower alkyl, hydroxy(lower)alkyl or oxo, provided that at least one of L and M is not hydrogen atom and that the five-membered ring may have one or two double bonds, $Q_1'$ and $Q_2'$ are hydrogen atom, halogen atom or lower alkyl, D is $-CH_2-CH_2-$, $-CH=CH-$, $-C\equiv C-$ or $-CO-CH_2-$, E is $-CH_2-CH_2-$ or $-CH=CH-$, W is $-CH_2-CH_2-CH_2-$, $-CH=CH-CH_2$ or $-CH_2-CH=CH-$, Ra' is hydrogen atom, lower alkyl, cyclo(lower)alkyl, monocyclic aryl, monocyclic aryl(lower)alkyl or monocyclic aroyl(lower)alkyl, Rb' is single bond or lower alkylene, Rc' is lower alkyl which is unsubstituted or substituted with halogen, lower cycloalkyl which is unsubstituted or substituted with lower alkyl, monocyclic aryl which is unsubstituted or substituted with halogen or halo(lower)alkyl, or monocyclic aryloxy which is unsubstituted or substituted with halogen or halo(lower)alkyl, or a pharmaceutically acceptable salt when $R_1$ is hydrogen atom.

In the above formula, the term "unsaturated" in the definitions for $R_1$ and $R_2$ is intended to include at least one and optionally more than one double bond and/or triple bond isolatedly, separately or serially present between carbon atoms of main and/or side chain. According to usual nomenclature, an unsaturation between two serial positions is represented by denoting younger number of said two positions, and an unsaturation between two distal positions is represented by denoting both of the positions. Preferred unsaturation is a double bond at position 2 and a double or triple bond at position 5.

The term "lower or medium aliphatic hydrocarbon residue" refers to a straight or branched chain hydrocarboyl group having 1 to 14 carbon atoms (for a side chain, 1 to 3 carbon atoms being preferred) and preferably 2 to 8 carbon atoms for $R_1$ and 2 to 10 carbon atoms for $R_2$.

The term "halo" denotes fluoro, chloro, bromo and iodo.

The term "lower" is intended to include a group having 1 to 6 carbon atoms unless otherwise specified.

The term "lower alkyl" as a group or a moiety in hydroxy(lower)alkyl includes saturated and straight or branched chain hydrocarbon radicals containing 1 to 6, preferably 1 to 5 and more preferable 1 to 4 carbon atoms, such as methyl, ethyl, propyl, isopropyl, butyl, isobutyl, t-butyl, pentyl and hexyl.

The term "lower alkoxy" refers to the group lower-alkyl-O- wherein lower alkyl is as defined above.

The term "lower alkylene" refers to the group obtainable by removing a hydrogen atom from the lower alkyl group as defined above and includes e.g. methylene, ethylene, propylene, tetramethylene, 2-methyltetramethylene, pentamethylene, hexamethylene etc.

The term "halo(lower) alkyl" refers to lower alkyl group as defined above which is substituted with at least one and preferably 1 to 3 halogen atoms as defined above and includes e.g. chloromethyl, bromomethyl, fluoromethyl, trifluoromethyl, 1,2-dichloromethyl, 1,2,2-trichloroethyl, chloropropyl, chlorobutyl, chloropentyl, chlorohexyl etc.

The term "hydroxy(lower)alkyl" refers to alkyl as defined above and substituted with at least one hydroxy group, such as hydroxymethyl, 1-hydroxyethyl, 2-hydroxyethyl and 1-methyl-1-hydroxyethyl.

The term "lower alkanoyloxy" refers to a group of the formula: RCO—O— wherein RCO— is an acyl group formed by oxidation of a lower alkyl group as defined above, e.g. acetyl.

The term "cyclo(lower)alkyl" refers to a cyclic group formed by cyclization of a lower alkyl group as defined above.

The term "aryl" includes unsubstituted or substituted aromatic carbocyclic or heterocyclic (preferably monocyclic) groups, e.g. phenyl, tolyl, xylyl and thienyl. Examples of substituents are halo and halo(lower) alkyl wherein halo and lower alkyl being as defined above.

The term "aryloxy" refers to a group of the formula: ArO- wherein Ar is aryl as defined above.

The term "monocyclic aryl" includes phenyl unsubstituted or substituted with lower alkyl substituents, e.g phenyl, tolyl, xylyl, cumenyl etc.

The term "monocyclic aryloxy" refers to a group of the formula: m.Aro- wherein mAr is monocyclic aryl as defined above and includes e.g. phenoxy, tolyloxy, cumenyloxy etc.

The term "monocyclic aryl(lower)alkyl" refers to a group consisting of monocyclic aryl and lower alkyl, both as defined above, combined together, and includes, for example, benzyl, phenethyl, tolylmethyl etc.

The term "monocyclic aroyl(lower)alkyl" refers to a group consisting of monocyclic aroyl such as benzoyl unsubstituted or substituted with lower alkyl substituent and lower alkyl as defined above combined together, and includes phenacyl(benzoylmethyl), toluoylmethyl, xyloylmethyl, etc.

The term "functional derivative" of carboxy as A includes salts (preferably pharmaceutically acceptable salts), esters and amides.

Suitable "pharmaceutically acceptable salt" includes conventional non-toxic salt, and may be a salt with an inorganic base, for example a metal salt such as an alkali metal salt (e.g. sodium salt, potassium salt, etc.) and an alkaline earth metal salt (e.g. calcium salt, magnesium salt, etc.), ammonium salt, a salt with an organic base, for example, an amine salt (e.g. methylamine salt, dimethylamine salt, cyclohexylamine salt, benzylamine salt, piperidine salt, ethylenediamine salt, ethanolamine salt, diethanolamine salt, triethanolamine salt, tris(hydroxymethylamino)ethane salt, monomethylmonoethanolamine salt, procaine salt, caffeine salt, etc.), a basic amino acid salt (e.g. arginine salt, lysine salt, etc.), tetraalkylammonium salt and the like. These salts can be prepared by the conventional process, for example from the corresponding acid and base or by salt interchange.

Examples of the esters are aliphatic esters, for example, $C_{1-6}$ alkyl ester such as methyl ester, ethyl ester, propyl ester, isopropyl ester, butyl ester, isobutyl ester, t-butyl ester, pentyl ester, 1-cyclopropylethyl ester, etc., lower alkenyl ester such as vinyl ester, allyl ester, etc., lower alkynyl ester such as ethynyl ester, propynyl ester, etc., hydroxy(lower) alkyl ester such as hydroxyethyl ester, lower alkoxy(lower)-alkyl ester such as methoxymethyl ester, 1-methoxyethyl ester, etc., and aromatic esters, for example, optionally substituted aryl ester such as phenyl ester, tolyl ester, t-butylphenyl ester, salicyl ester, 3,4-di-methoxyphenyl ester, benzamidophenyl ester etc., aryl(lower)alkyl ester such as benzyl ester, trityl ester, benzhydryl ester, etc. Examples of the amides are mono- or di- lower alkyl amides such as methylamide, ethylamide, dimethylamide, etc., arylamide such as anilide, toluidide, and lower alkyl- or aryl-sulfonylamide such as methylsulfonylamide, ethylsulfonylamide, tolylsulfonYlamide etc.

Preferred examples of A include —COOH, —COOCH$_3$, —COOCH$_2$CH$_3$, —COOCH(CH$_3$)$_2$ and —CONHSO$_2$CH$_3$.

Examples of preferred R$_1$ are —(CH$_2$)$_2$—, —(CH$_2$)$_6$—, —CH$_2$CO(CH$_2$)$_2$—, —CH$_2$CH=CH(CH$_2$)$_3$—, —CH$_2$CO(CH$_2$)$_4$—, —(CH$_2$)$_2$CH=CH(CH$_2$)$_2$—, —(CH$_2$)$_4$CH=CH—, —CH$_2$CH=C=CH(CH$_2$)$_2$— etc.

Examples of preferred R$_2$ are —(CH$_2$)$_2$CO(CH$_2$)$_4$—CH$_3$, —(CH$_2$)$_2$CO(CH$_2$)$_4$—COOH, —(CH$_2$)$_2$COC(CH$_3$)$_2$(CH$_2$)$_3$—CH$_3$, —(CH$_2$)$_2$COCH$_2$O-phenyl, —(CH$_2$)$_2$COCH$_2$O-methachlorophenyl, —(CH$_2$)$_2$COCH$_2$O-methatrifluorophenyl, —(CH$_2$)$_2$COCH$_2$O-3-thienyl, —(CH$_2$)$_2$CO(CH$_2$)$_2$-phenyl, —(CH$_2$)$_2$COCH$_2$CH(CH$_3$)(CH$_2$)$_3$CH$_3$, —(CH$_2$)$_2$COC(CH$_3$)$_2$CH$_2$OCH$_2$CH$_3$, —(CH$_2$)$_2$COCH(CH=CH)(CH$_2$)$_3$CH$_3$, —(CH$_2$)$_2$CO-cyclopentyl, —(CH$_2$)$_2$CO-cyclohexyl, —(CH$_2$)$_2$CO(CH$_2$)$_2$-cyclohexyl, —(CH$_2$)$_2$COCH(CH$_3$)(CH$_2$)$_2$CH=C—(CH$_3$)$_2$, —(CH$_2$)$_2$COCH(CH$_3$)CH$_2$CC=CH, —CH=CHCO(CH$_2$)$_4$—CH$_3$, —CH=CHCOC(CH$_3$)$_2$(CH$_2$)$_3$—CH$_3$, —CH=CHCOCH$_2$O-phenyl, —CH=CHCO—CH$_2$O-methachlorophenyl, —CH=CHCOCH$_2$O-methatrifluorophenyl, —CH=CHCOCH$_2$O-3-thienyl, —CH=CHCO(CH$_2$)$_2$-phenyl, —CH=CHCOCH$_2$CH(CH$_3$)(CH$_2$)$_3$CH$_3$, —CH=CHCOC(CH$_3$)$_2$CH$_2$OCH$_2$CH$_3$, —CH=CHCOCH(CH=CH)(CH$_2$)$_3$CH$_3$, —CH=CHCO-cyclopentyl, —CH=CHCO—cyclohexyl, —CH=CHCOCH$_2$CH(CH$_3$)(CH$_2$)$_2$CH=C(CH$_3$)$_2$, —CH=CHCOCH(CH$_3$)CH$_2$CC=CH, —CH=CHCOCH(CH$_3$)(CH$_2$)$_4$CH$_3$ etc.

The configuration of the ring and α- and/or ω-chain in the above formulas (I) and (II) may be the same as or different from that in the natural prostaglandins. However, the present invention also include a mixture of a compound having natural configuration and that of unnatural configuration.

Examples of the typical compounds of the present invention are 15-keto-PGs and 13,14-dihydro-15-keto-PGs and their derivatives such as 6-oxo-derivatives, Δ$^2$-derivatives, 3R,S-methyl-derivatives, 5R,S-fluord-derivatives, 5,5-difluoro-derivatives, 16R,S-methyl-derivatives, 16,16-dimethyl-derivatives, 16R,S-fluoro-derivatives, 16,16-difluoro-derivatives, 17S-methyl-derivatives, 17R,S-fluoro-derivatives, 17,17-difluoro-derivatives, 19-methyl-derivatives, 20-methyl-derivatives, 20-ethyl-derivatives, 19-desmethyl-derivatives, 16-desbutyl-16-phenoxy-derivatives and 2-decarboxy-2-carboxyalkyl derivatives.

In the 15-keto-PG compounds used in the present invention, when the bond between 13- and 14-positions is saturated, a keto-hemiacetal equilibrium may sometimes be formed by the formation of a hemiacetal between the hydroxy group at 11-position and the keto group at 15-position.

When these tautomeric isomers are present, the ratio of the existing isomers will vary depending on the structure of other part of the molecule or the kind of possible substituents and in some cases one of the isomers is predominantly present. The present invention, however, includes both isomers, and while any compound of the invention may be represented by a structure or nomenclature of keto-type, this should be understood as a matter of mere convenience and should not be considered to be intended to exclude the compound in hemiacetal type isomer.

In the present invention, indivisional tautomeric isomers, a mixture thereof, or optical isomers, a mixture thereof, racemic mixture and other isomers such as stereoisomers can be used in the some purpose.

Some of the compounds used in the present invention are novel and may be prepared by the method disclosed in Japanese Patent Publications A-64-52753, A-1-104040, A-1-151519, A-2-131446 etc. Alternatively, these compounds may be prepared by a process analogous to that described herein or to known process.

A practical preparation of the 15-keto compounds involves the following steps; referring to the Synthetic Charts I to III, reaction of the aldehyde (2) prepared by the Collins oxidation of commercially available (—)-Corey lactone (1) with dimethyl (2-oxoheptyl)phosphate anion to give α,β-unsaturated ketone (3), reduction of the α,β-unsaturated ketone (3) to the corresponding saturated ketone (4), protection of the carbonyl group of the ketone (4) with a diol to the corresponding ketal (5), and deprotection of the p-phenylbenzoyl group to give the corresponding alcohol (6) followed by protection of the newly derived hydroxy group with dihydropyrane to give the corresponding tetrahydropyranyl ether (7). According to the above process, a precursor of PGEs wherein ω-chain is a 13,14-dihydro-15-keto-alkyl group is prepared.

Using the above tetrahydropyranyl ether (7), 6-keto-PGE$_1$s (15) of which a group constituted with carbon atoms at positions 5, 6 and 7 is —C$_7$H$_2$—C$_6$(O)—C$_5$-H$_2$—, may be prepared in the following steps; reduction of the tetrahydropyranyl ether (7) with, for example, diisobutyl aluminum hydride to give the corresponding lactol (8), reaction of the lactol (8), with the ylide generated from (4-carboxybutyl)triphenyl phosphonium bromide followed by esterification (10), cyclization between the 5,6-double bond and the hydroxyl group at 9-position with NBS or iodine to give the halogenated compound (11), dehydrohalogenation of the compound (11) with, for example, DBU to give the 6-keto compound (13) followed by Jones oxidation and removal of the protecting groups.

Furthermore, PGE$_2$s (19) of which a group constituted with carbon atoms positions 5, 6 and 7 is —C$_7$H$_2$—C$_6$H=C$_5$H—may be prepared in the following steps; as shown in the Synthetic Chart II, reduction of the above tetrahydropyranyl ether (7) to give the lactol (8), reaction of the resultant lactol (8) with the ylide derived from (4-carboxybutyl-)triphenyl phosphonium bromide to give the carboxylic acid (16) followed by esterification to give ester (17), Jones oxidation of the esters (17) to give the compound (18), and removal of the protecting groups.

Using the above the tetrahydropyranyl ether (7) as the starting material the compound having —C$_7$H$_2$—C$_6$H$_2$—C$_5$H$_2$— may be prepared by using the same process as that for preparing PGE$_2$ having —CH$_2$CH=CH— and subjecting the resultant compound (18) to catalytic reduction for reducing the double bond between the positions 5 and 6 followed by removal of the protective groups.

Synthesis of 5 6-dehydro-PGE$_2$s having —C$_7$H$_2$—C$_6$≡C$_5$—may be carried out by capturing a copper enolate formed by 1,4-addition of a monoalkylcopper complex or a dialkylcopper complex of the following formulae:

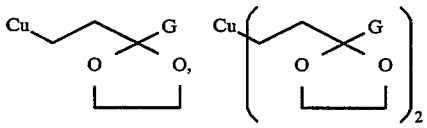

wherein G is alkyl to 4R-t-butyldimethylsilyloxy-2-cyclopenten-1-one with 6-alkoxycarbonyl-1-iodo-2-hexyne or the derivatives.

The 11β type PGEs can be prepared according to the Synthetic Chart III.

PGE derivatives having methyl group at position 11 in place of hydroxy can be prepared by reacting a dimethyl copper complex with PGA-type compound obtained by subjecting 9-hydroxy-11-tosylate to the Jones oxidation. Alternatively, they can be prepared by protecting carbonyl of saturated ketone (4) produced by reduced by reducing unsaturated ketone (3), eliminating p-phenylbenzoyl and tosylating the produced alcohol, treating with DBU to form a lactol, introducing the alpha-chain by Wittig reaction, oxidizing the alcohol at 9-position to give PGA-type compound, and reacting the product with dimethyl copper complex in order to introduce a methyl group into position 11 to give 11-methyl-PGE-type compound, which on reduction with e.g. sodium borohydride gives 11-methyl-PGF-type compound. 11-hydroxymethyl-PGE-type compound, is obtained by a benzophenone-sensitized photoaddition of methanol of PGA-type compound, which is reduced with e.g. sodium borohydride to give 11-hydroxymethyl-PGF-type compound. The 16-mono- or 16,16- dihalo type PGEs can be prepared according to the Synthetic Chart IV. The synthetic route for the compounds used in the present invention is not limited to the above one and may vary using different protecting, reducing and/or oxidizating methods.

Furthermore, the novel compounds of the formula III may be prepared by the following process, as summarized in Synthetic Charts V to VII, wherein P1, P2, P3, P4, P5, P6, P7, P8, Pa, Pb, Pc and Pd are protective groups, R'a is lower alkyl and Rb and Rc are the same as above.

Referring to Synthetic Chart V, a protected Corey lactone (40) (commercially available) having a suitable protective group (e.g. 4-phenylbenzoyl) is oxidized (e.g. by Collins oxidation) and the produced aldehyde (41) is reacted with (2-oxoalkyl) phosphonic acid ester having desired R2 and R3 groups to give the compound (42). The oxo group is reduced to form (43), which is converted into (44) by protecting reaction. The acyl group at position 11 is removed to produce (45), to which another protective group (e.g. tetrahydropyramyl) is introduced to give (46). The lactone ring is opened with alkali to form a carboxylic acid which, on esterification, gives (47). A protective group (e.g. tetrahydropyranyl) is introduced into (47) to give (48). After reducing the ester group by a reducing agent (e.g. by isobutylaluminum hydride) into an aldehyde group, the produced compound is reacted with an α-chain introducing agent (f) in the presence of a basic condensing agent (e.g. litium isopropyl amide) to form (49), of which the terminal group in α-chain is deprotected to produce (50). The obtained alcohol is oxidized (e.g. by Collins oxydation) and then esterified to give (51) and the group at position 5 is decarboxylated to afford (52). A protective group is removed by a method according to the nature of said group to form (53), which is reduced (e.g. catalytically) to form (54), which, on oxidation (e.g. by Collins oxidation) of position 15 gives (55). Deprotection of (55) produces (56), which, after protecting position 11 alone, is oxydized (e.g. by Collins oxydation) to give (57). This is deprotected to afford the desired (58). In the above process, when the reduction of (53) to (54) is omitted, an unsaturated compound is obtained. A compound wherein Ra is hydrogen can be obtained by hydrolyzing the compound (58).

The α-chain introducing agent (f) is prepared by a process shown in Synthetic Chart V. Thus, E-caprolactone (a) is ring-opened by an alcohol which can form the carboxy protective group Pa to give (b). The hydroxy group is protected to give (c), which is decarboxylated to (d), halogenated to (e) and then subjected to halogen exchange reaction to afford the compound (f).

In another process referring to Synthetic Chart VI, the protected Corey lactone (40) is converted into the compound (59) by reaction steps similar to that from (1) to (7) in synthetic Chart I. The compound (59) is hydrolyzed by alkali (e.g. sodium or potassium hydroxide) to form the free acid (60), which is esterified (e.g. with diazomethane) to give (61). After protecting the hydroxy group at position 9 giving (62), the ester group is reduced (e.g. by lithium aluminum hydride) to produce an alcohol (63) and newly formed hydroxy group is oxidized (e.g. by Swan oxidation) to an aldehyde (64). The aldehyde is reacted with an α-chain introducing agent (i) in the presence of zinc dust and mercuric chloride under ultrasonic irradiation to produce the compound (65). This is deprotected to form (66) and hydrogenated (e.g. over Pd/C) to afford (67), which is then oxidized in two steps (e.g. swan oxidation and Jone's oxidation), via(68), to give (69). The acid (69) is deprotected either directly to (71) or via ester (70) to (72).

The α-chain introducing agent (i) is prepared by a process shown is synthetic Chart VIII. Thus, the acetylenic alcohol (g) is protected to form (h), which is reacted with difromodifluoromethane to produce (i).

Referring to Synthetic Chart V, the compound (73) (for example, a compound wherein Q₁' and Q₂' are hydrogen is the compound 8 described in Synthetic Chart I on page 37 of JP-A-52753/1989) is reacted with a ylid produced from (6-carboxyhexyl)triphenylphosphonium bromide to form the compound (74), which is esterified to give the compound (75), which, on removal of the protective groups, can give the compound (76). Also, referring to Synthetic Chart VI, the above compound (75) is oxidized by Jones oxidation to form the compound (77), which can be given the compound (78) by removing the protective groups. The compounds wherein W is —CH=CH—CH₂— or —CH₂—CH=CH— can be prepared by reacting the compound (73) with a ylid produced from (6-carboxy-2-hexenyl)triphenylphosphonium bromide or (6-carboxy-3-hexenyl)-triphenylphosphonium bromide, respectively, and the treating the formed compound in a manner similar to that above.

In another example, referring to Synthetic Chart VII, the compound (80), obtained by deprotecting the compound (79) which is commercially available, is oxidized by Swern oxidation to give the aldehyde (81), which is reacted with 2-oxoheptyl phosphonate (for example, 3,3-dihalogenated derivative) to give the compound (82). Catalytic reduction of it gives the compound (83), the ketone moiety of which is reduced by sodium borohydride to form the compound (84). This is further reduced by diisobutylaluminum hydride to give the lactol (85). On reaction with carboxyhexylphosphonium bromide, it gives the compound (86), which is esterified to the compound (87), oxidized to the compound (88) and deprotected to the compound (78). If desired, this can be hydrolyzed to the free acid (89). Also, in the Synthetic Chart VIII, the above compound (87) can be catalytically hydrogenated to form the compound (90), which is oxidized by Swern oxidation to give the compound (91) and then deprotected to form the desired compound (92).

In the above process, when the reduction in the step from the compound (82) to the compound (73) is omitted, a compound wherein Z is —CH=CH— is obtained.

Further, when the compounds of the formula (I) wherein L is other than OH (for example, lower alkyl) are desired, the lactone moiety in the compound obtained by removing the protective group at position 11 and introducing a protective group in position 15 of the compound (84) is reduced to lactol and then an α-chain is introduced to the product by Wittig reaction. Then the hydroxy group at position 11 is protected by a lower alkane- or monocyclic aryl-sulfonate group and the product is subjected to oxidation (for example, Jones) to give 10-en-9-one compound, which is reacted with lower alkyl lithium to form a 11-lower alkyl compound. Compounds of PGD-type can be obtained by oxidizing the 11-deprotected compounds. Compounds of PGA-type can be obtained from the 10-en-9-one compounds. In addition, as shown in Synthetic Chart IX, 6-keto compounds can be obtained by reacting the compound (75) with N-bromosuccinimide or iodine to form the compound (93), followed by treatment with DBU. The 5,6-dehydro (i.e. acetylenic) compounds can be prepared, according to Synthetic Chart X, by reacting the copper enolate, formed by reacting the compound (95) with a copper complex, with 8-alkoxycarbonyl-1-iodo-2-octyne. Saturated α-chain introducing agent are prepared as shown in Synthetic Chart XI.

In a further example, according to Synthetic Chart XII, the hydroxy group at position 15 of the compound (84) is protected (for example, by silyl protective group) to form the compound (97) and lactone moiety of which is reduced to lactol giving the compound (98), which is then reacted with an α-chain introducing agent (for example, a ylid produced from (6-carboxyhexyl)triphenyl phosphonium bromide) to give the compound (99). Then the carboxy group is protected to form the compound (100) and the hydroxy group at position 9 is protected to form the compound (101). The protective group at position 15 is removed to give the compound (101), which is oxidized to the compound (102). Deprotection at positions 9 and 11 gives the desired compound (104).

Further, as shown in Synthetic Chart XIII, the compound (86) obtained as in Synthetic Chart VII is protected with a protective group removable by catalytic hydrogenation (for example, benzyl) to form the compound (87), which is oxidized at position 9 and deprotected at position 11 to give the compound (78). Catalytic hydrogenation of this compound gives the desired compound (105).

Corresponding other PG compounds can be produced analogously.

Synthetic Chart I

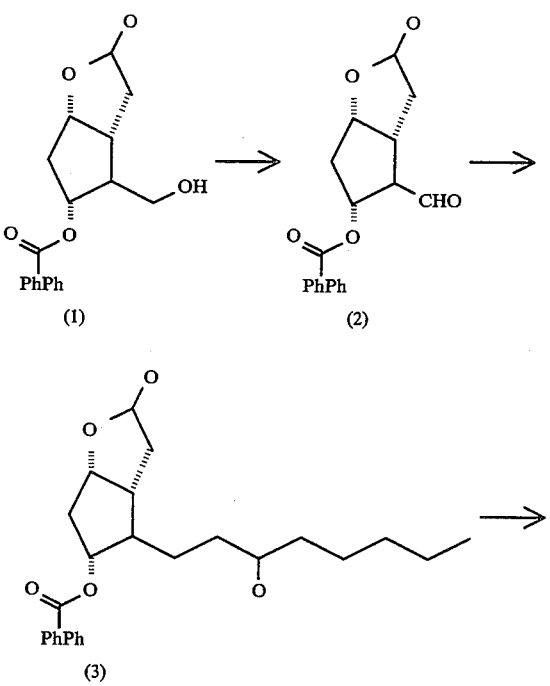

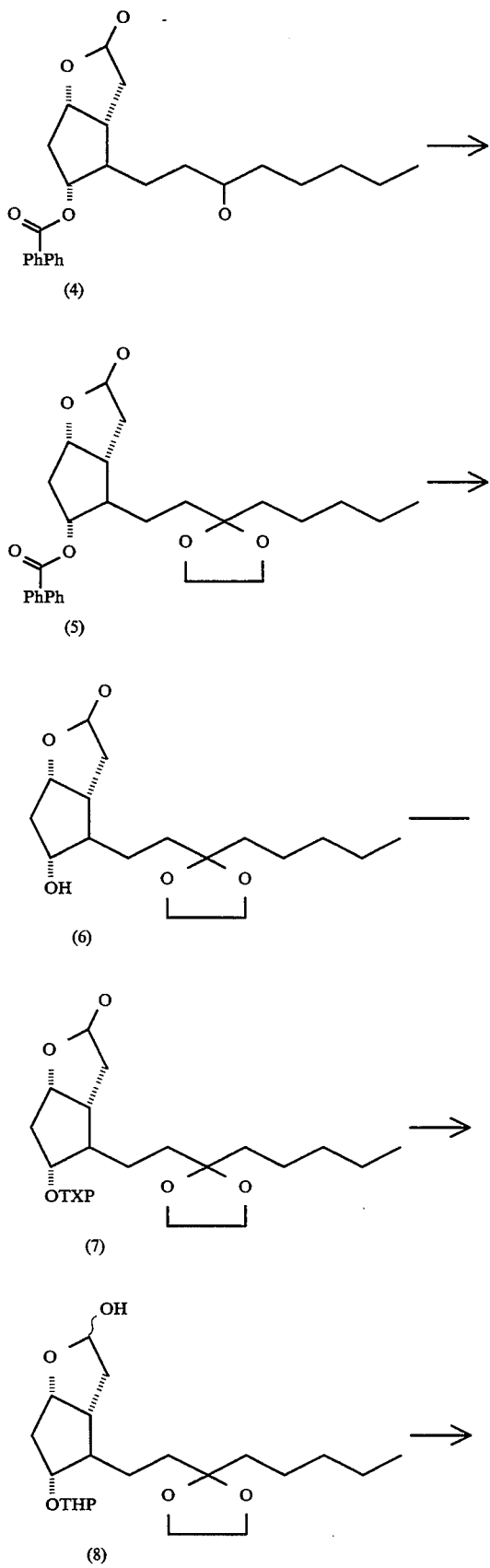
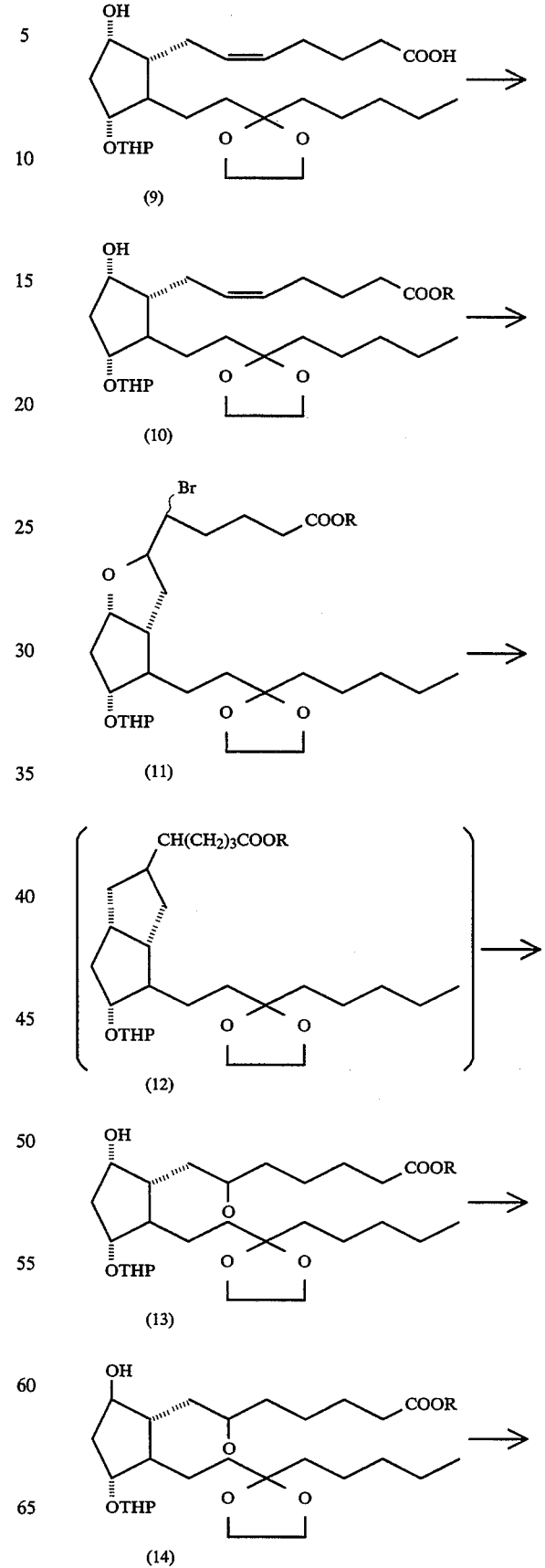

-continued
Synthetic Chart I
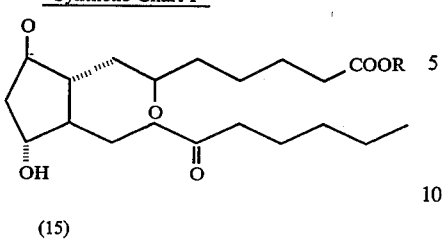
(15)
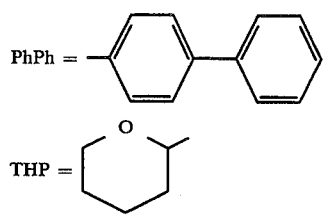
R = lower alkyl
Synthetic Chart II
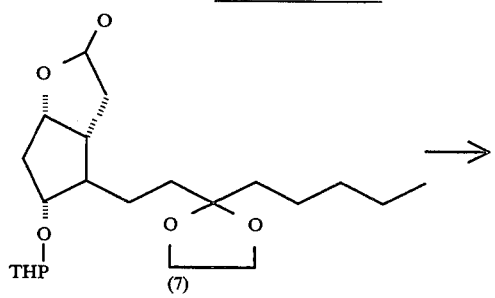
(7)
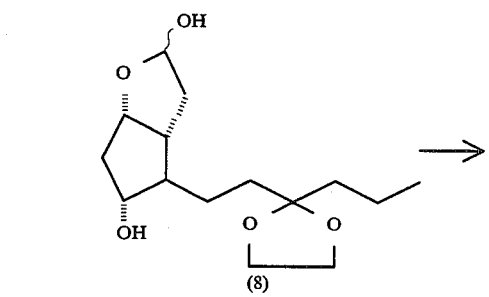
(8)
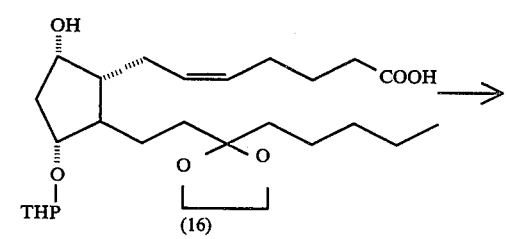
(16)
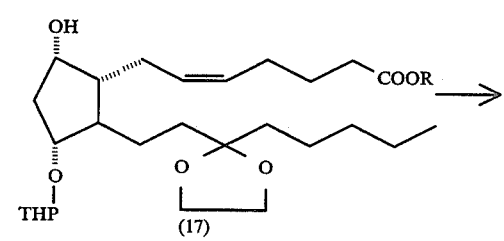
(17)
-continued
Synthetic Chart II
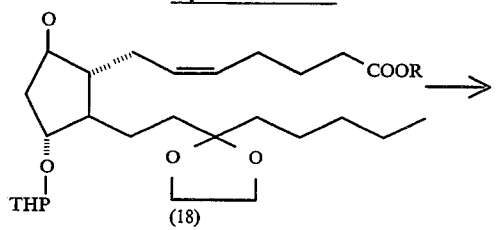
(18)
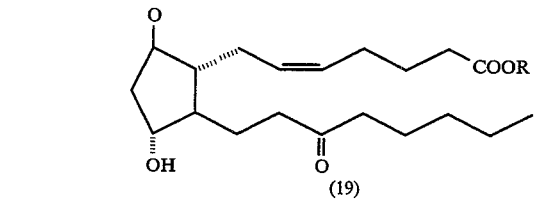
(19)
Synthetic Chart III
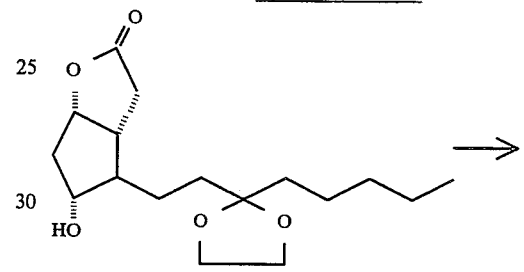
(6)
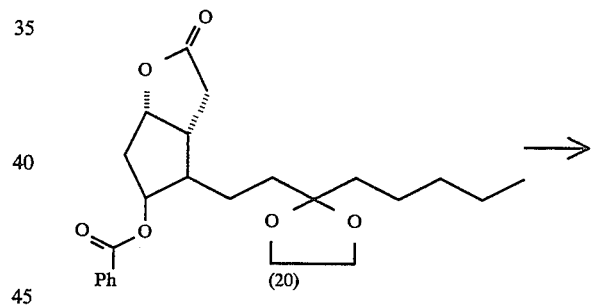
(20)
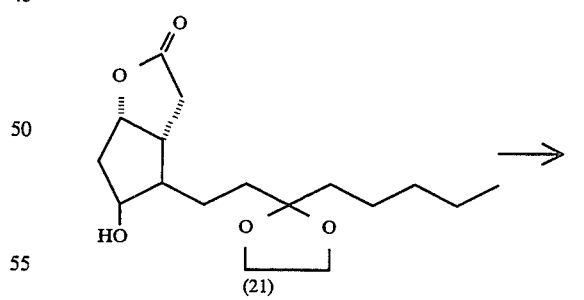
(21)
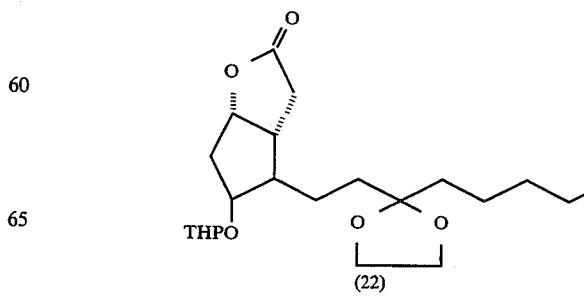
(22)

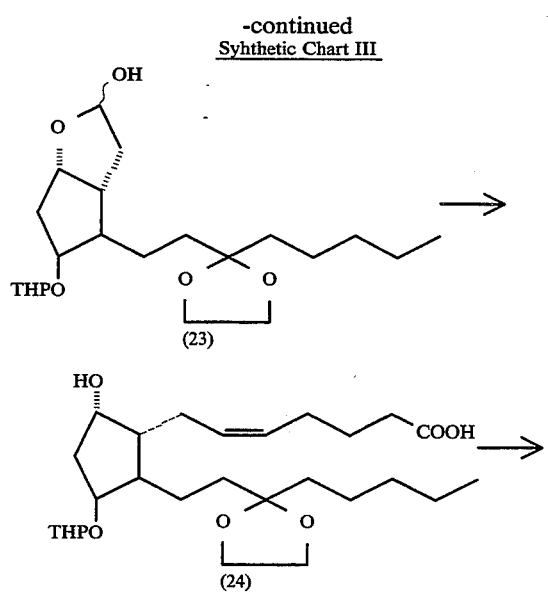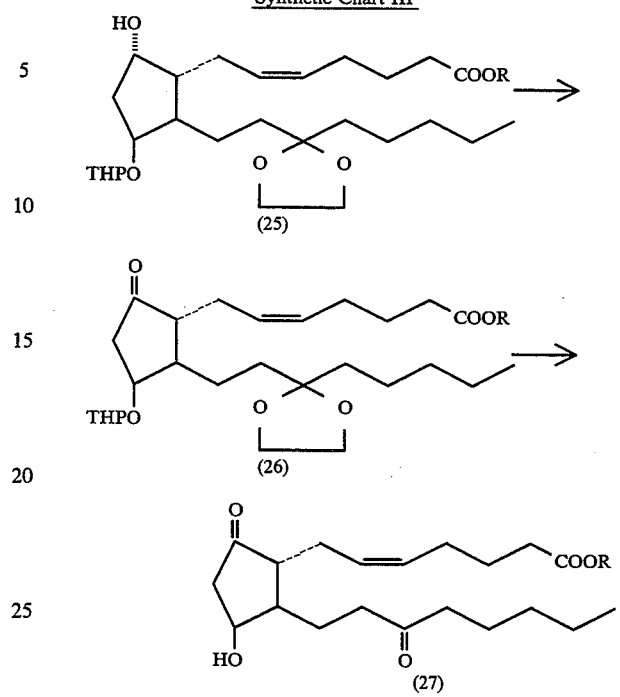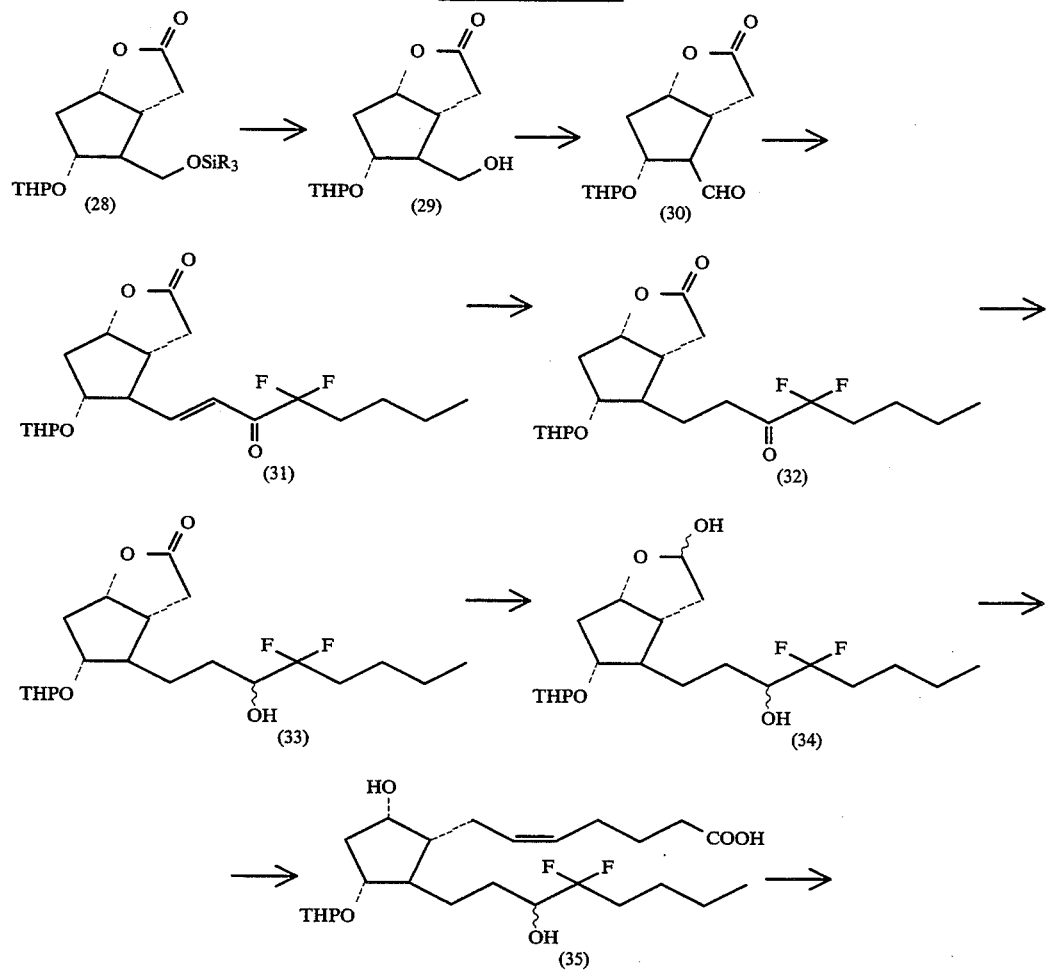

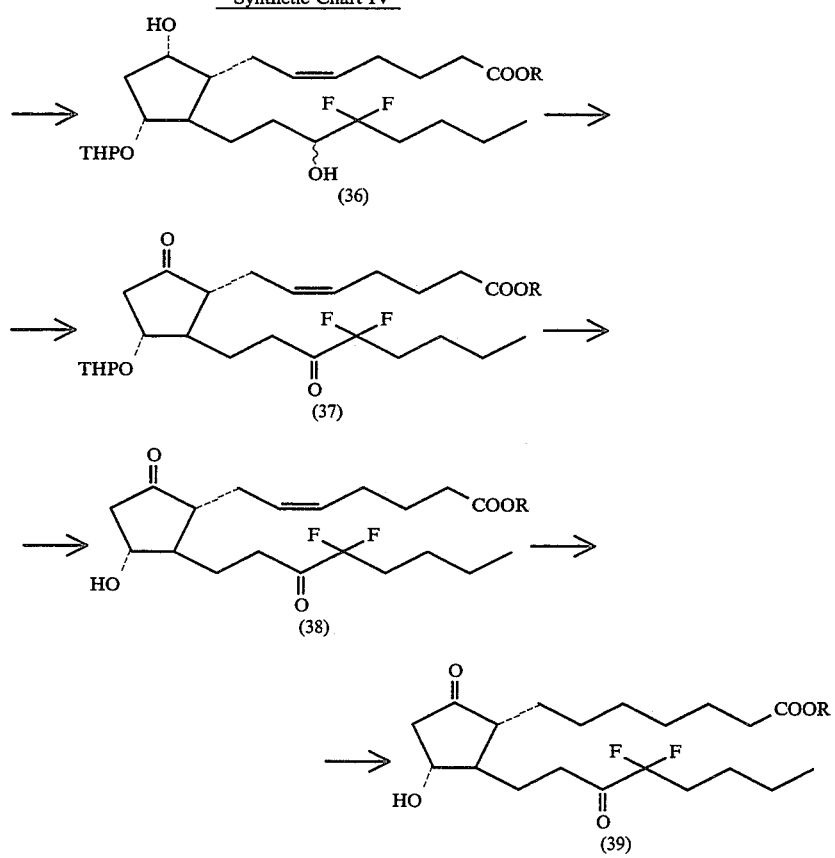
-continued
Synthetic Chart IV
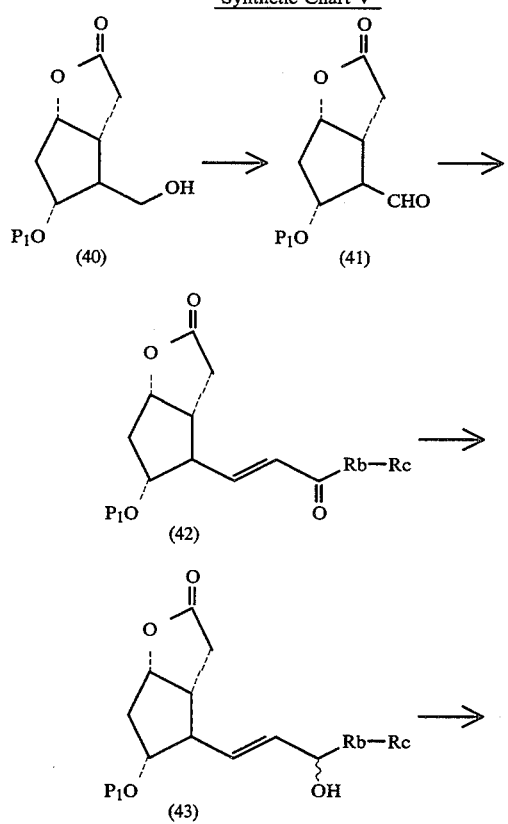
Synthetic Chart V
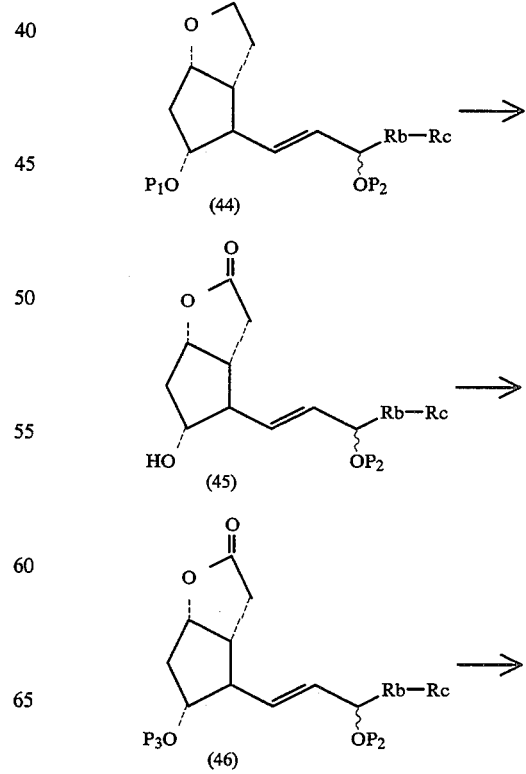
-continued
Synthetic Chart V

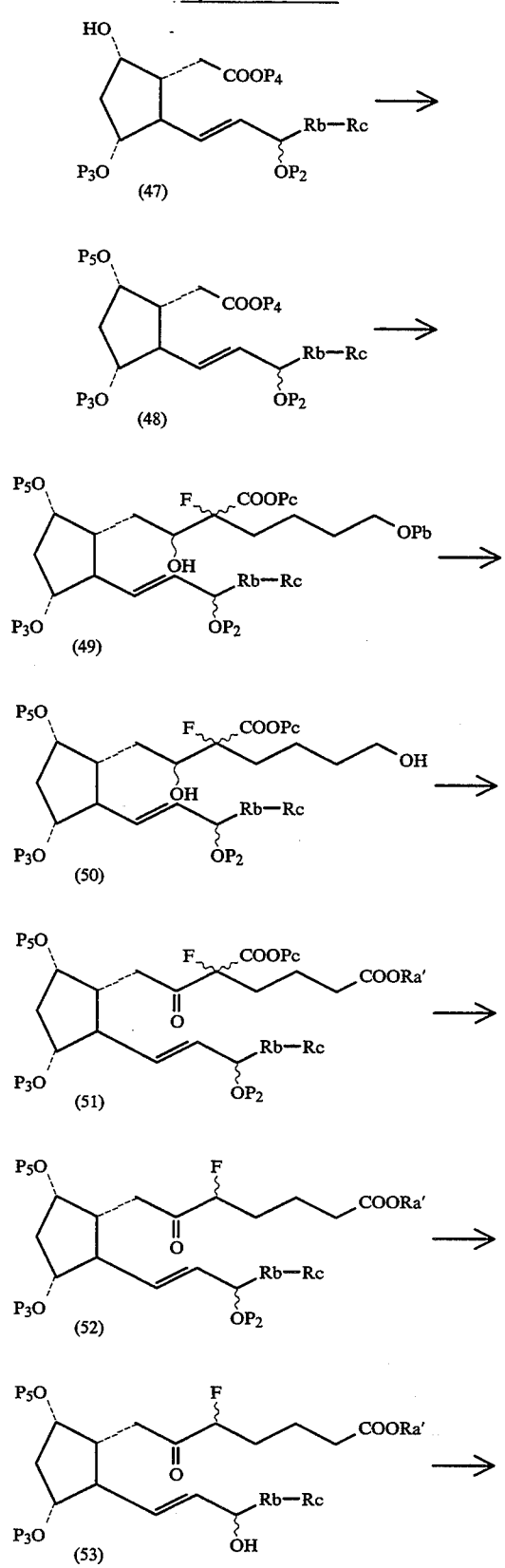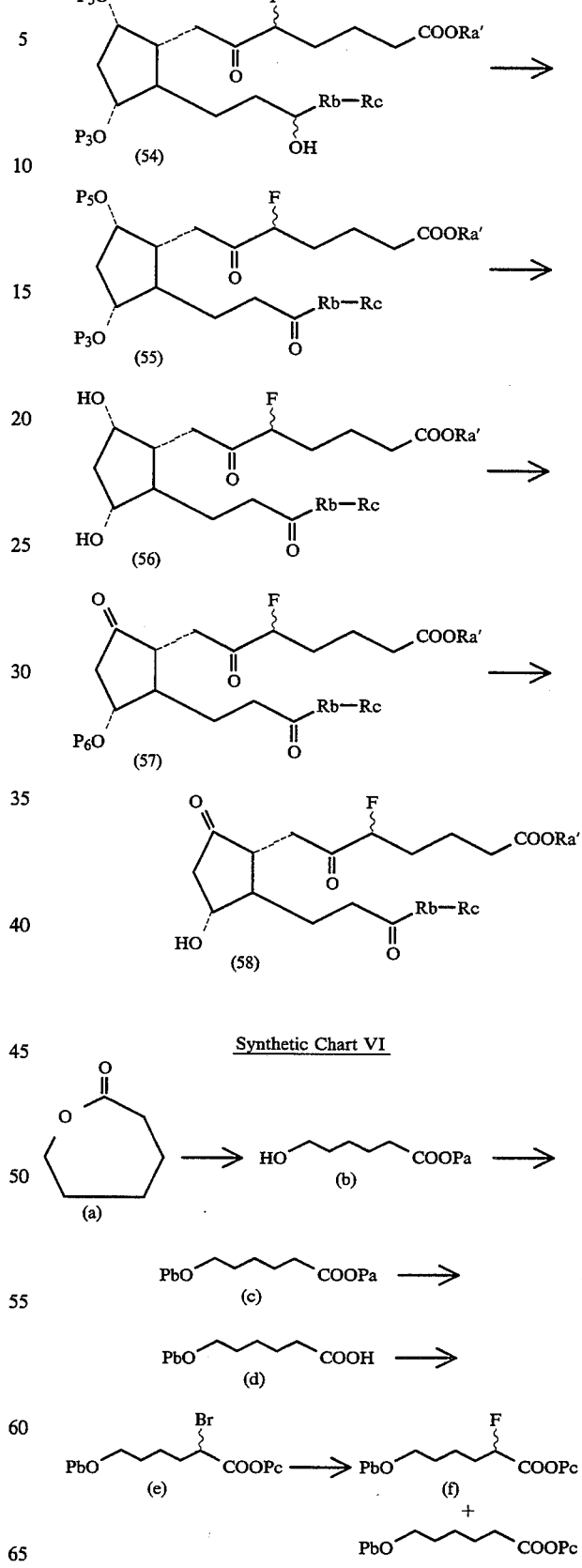

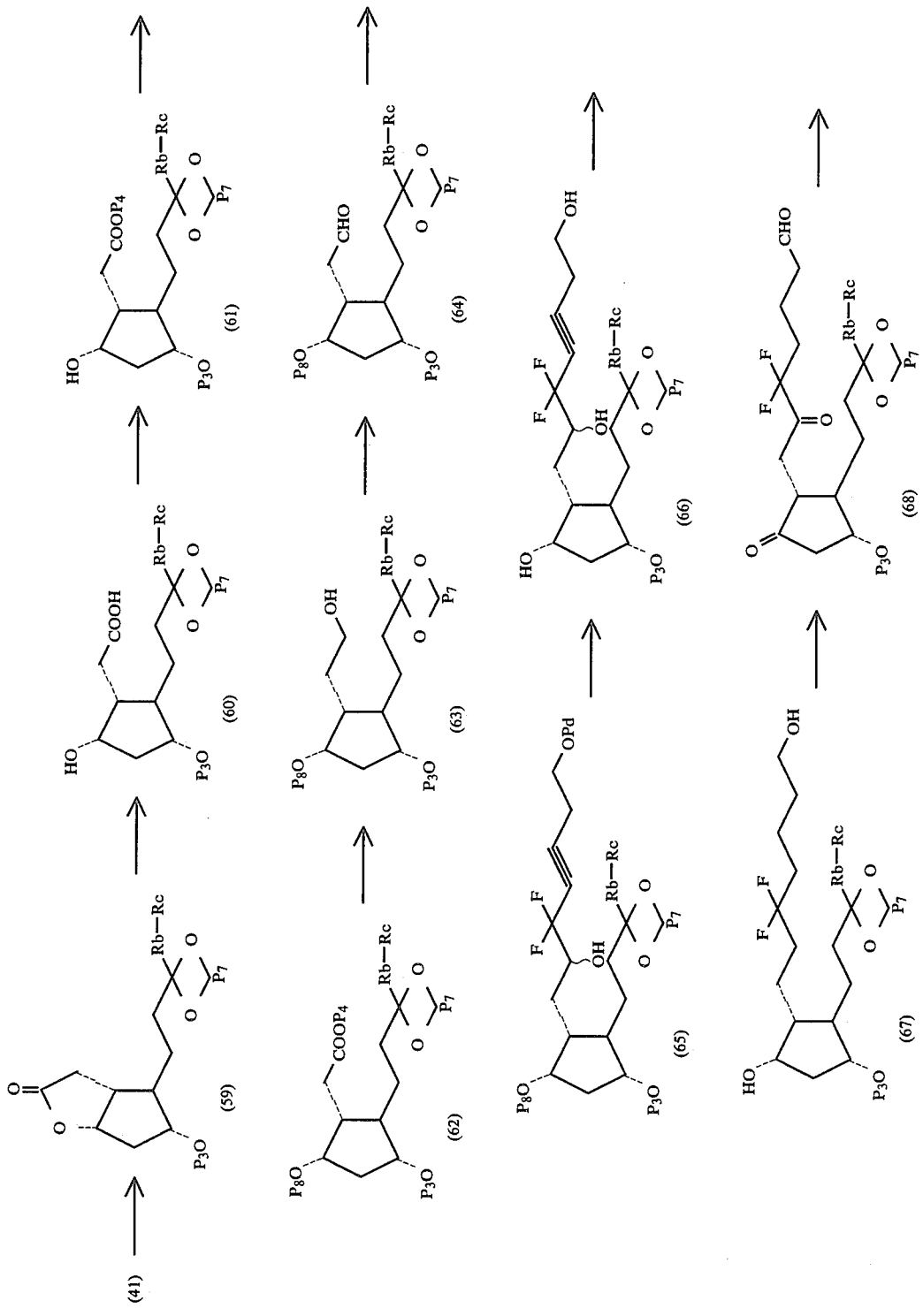
Synthetic Chart VII

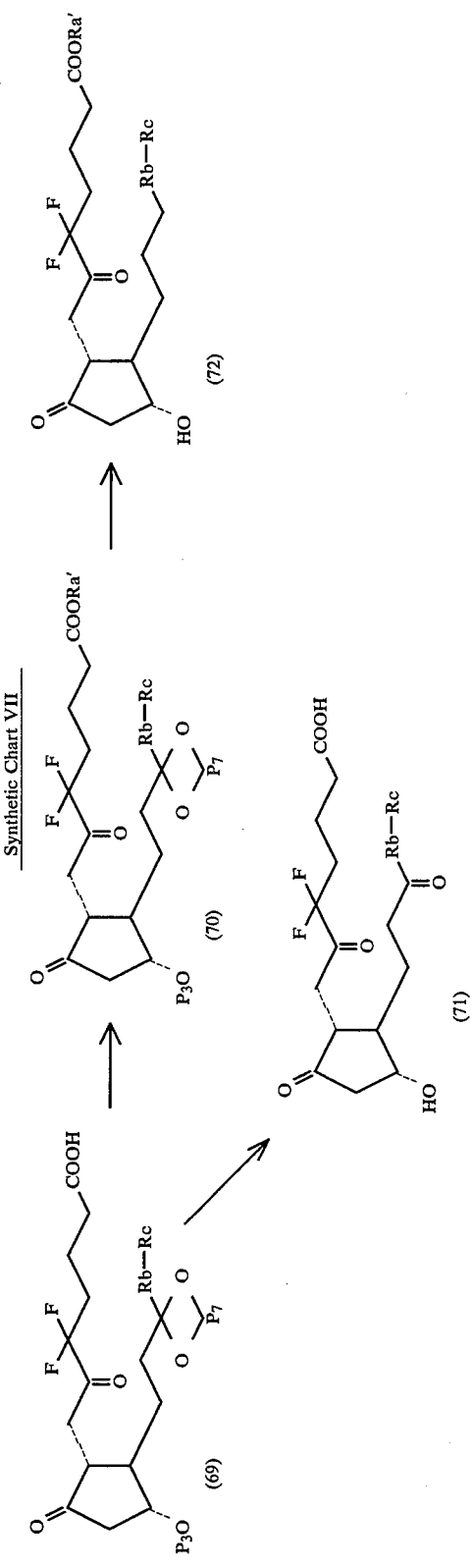

Synthetic Chart VIII
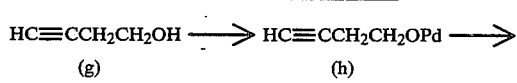
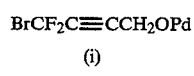
Synthetic Chart IX
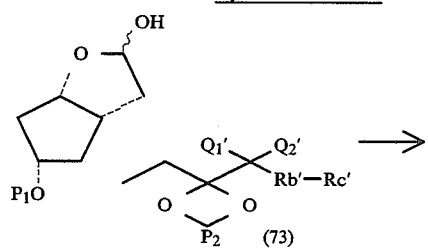
(73)
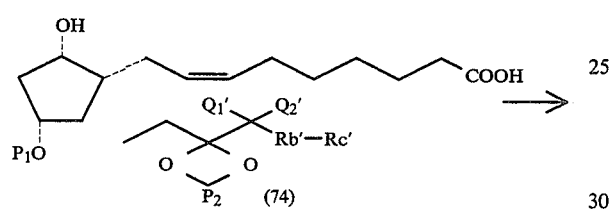
(74)
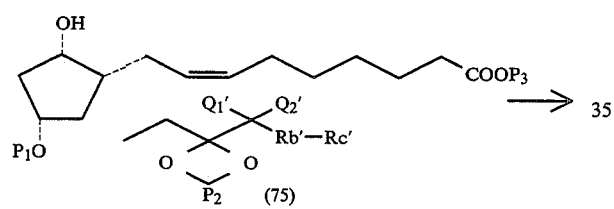
(75)
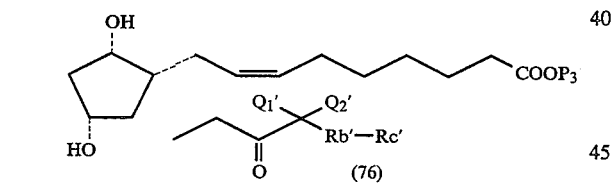
(76)
Synthetic Chart X
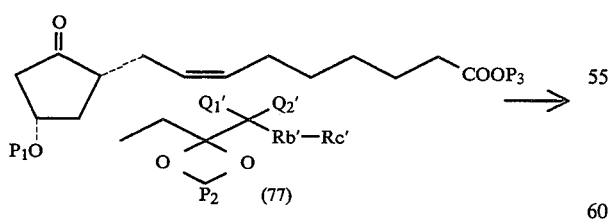
(77)
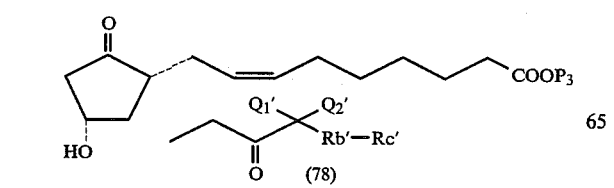
(78)
Synthetic Chart XI
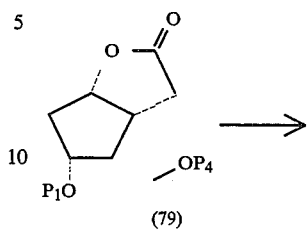
(79)
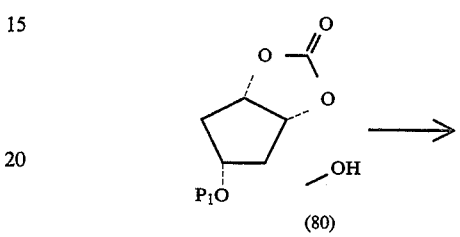
(80)
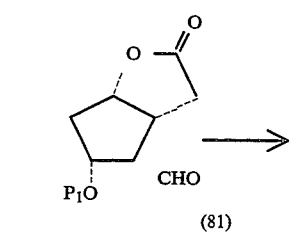
(81)
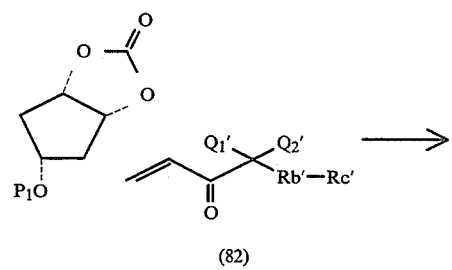
(82)
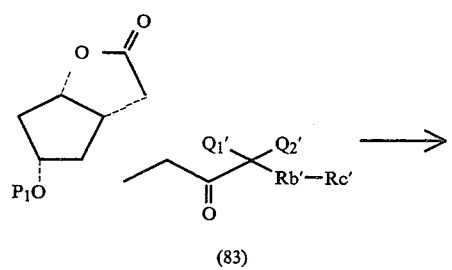
(83)
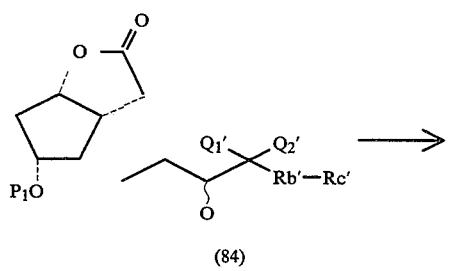
(84)

-continued
Synthetic Chart XI
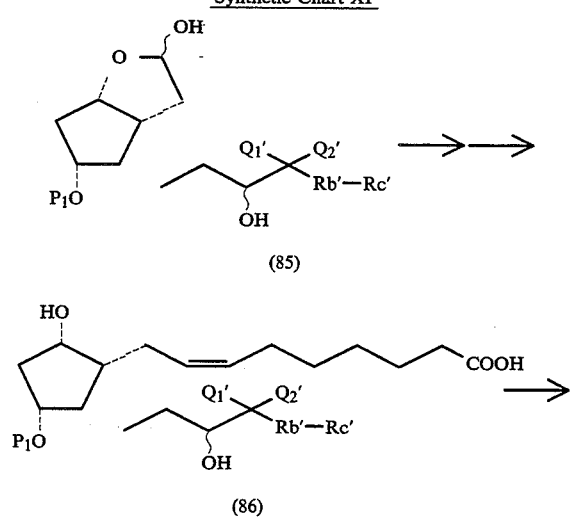
→(78)
Synthetic Chart XII
(87) →
-continued
Synthetic Chart XII
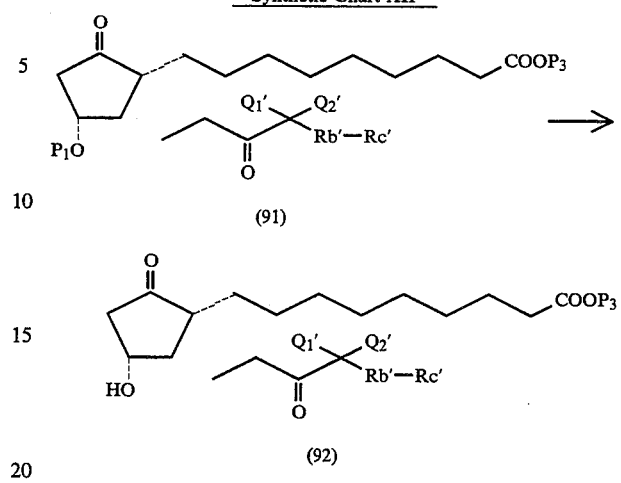
Synthetic Chart XIII
(75) →
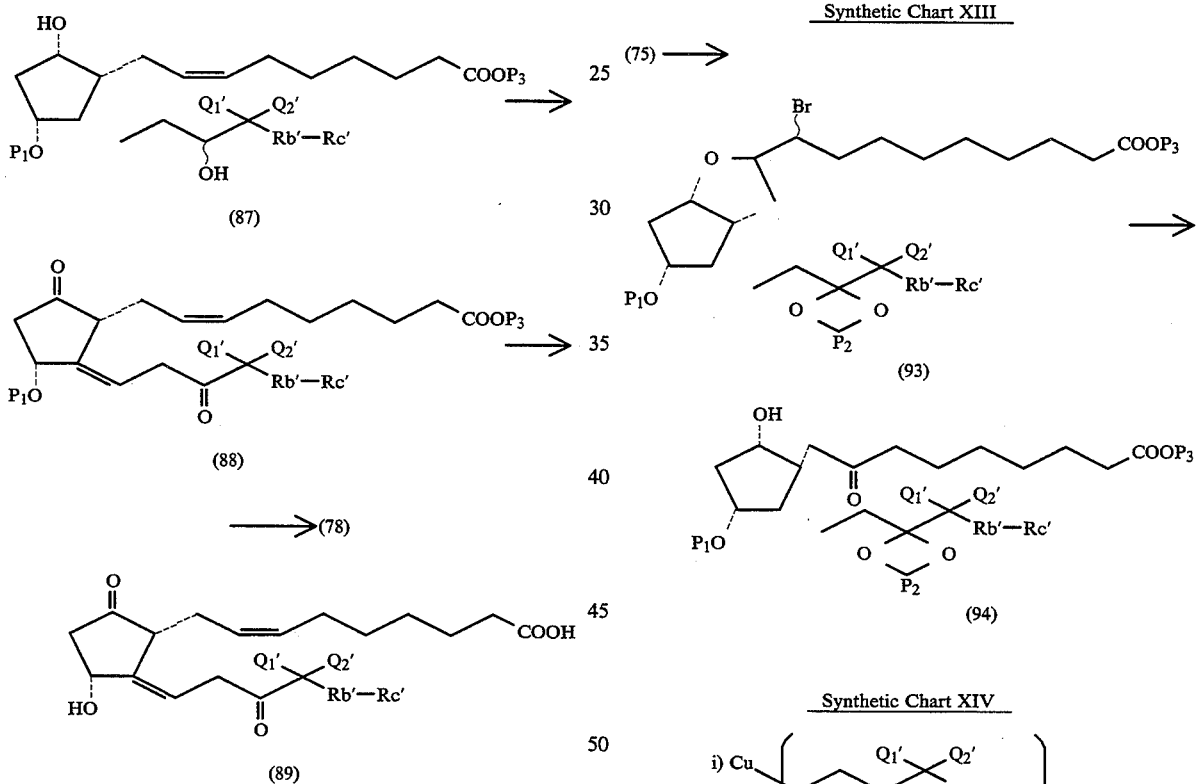
Synthetic Chart XIV
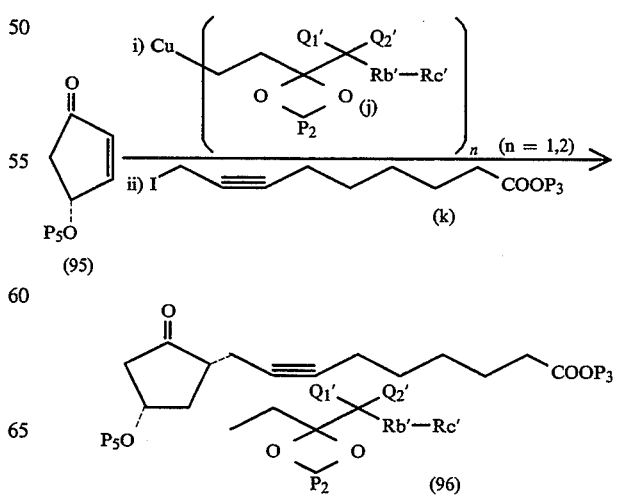

Synthetic Chart XV

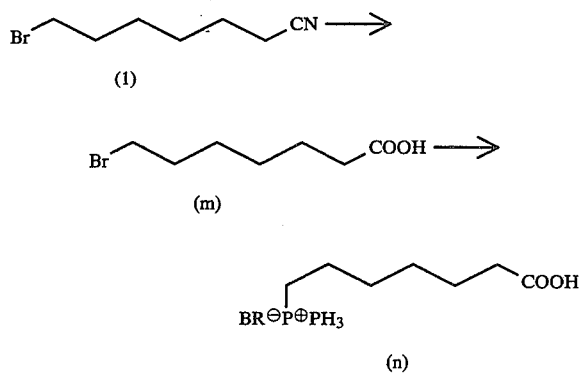

Synthetic Chart XVI

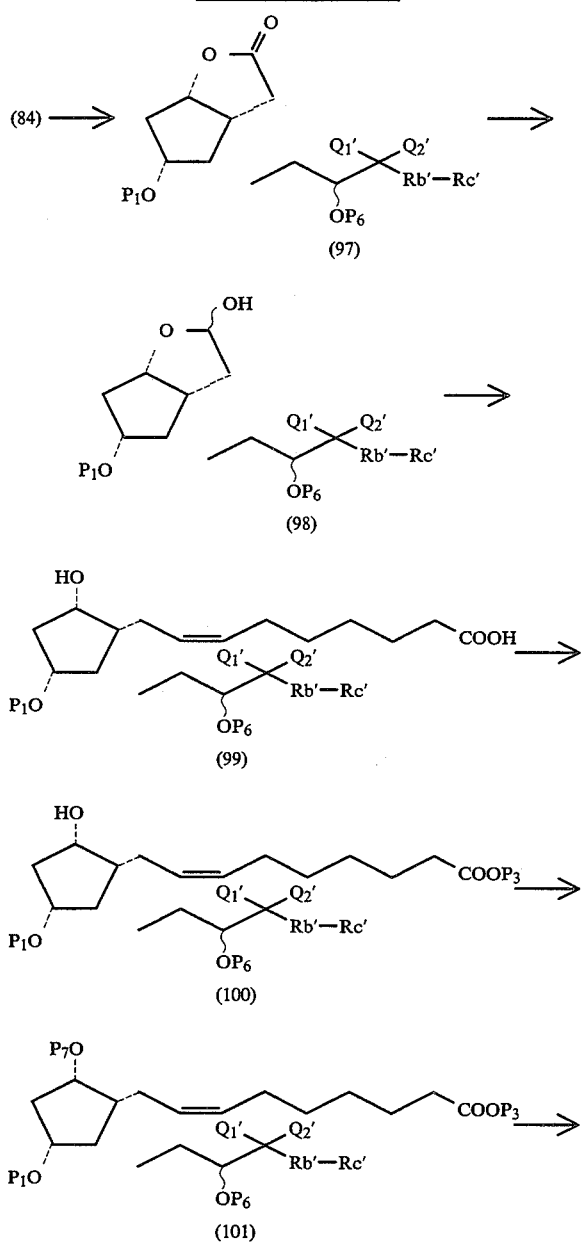

Synthetic Chart XVI -continued

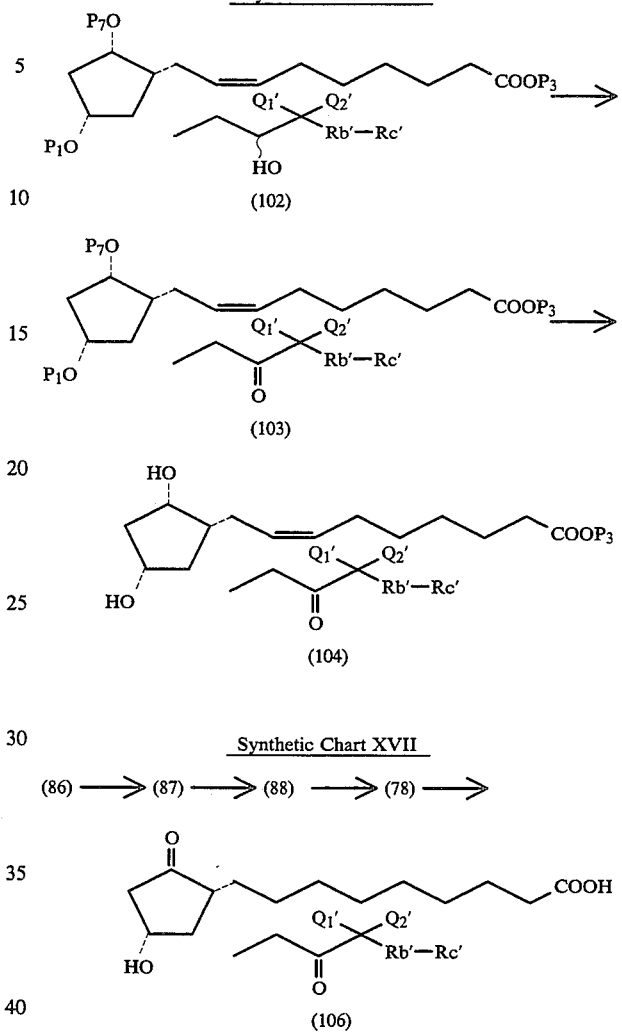

Synthetic Chart XVII

(86) ⟶ (87) ⟶ (88) ⟶ (78) ⟶

Since the above 15-keto-PG compounds have action inhibiting inflammatory reaction, they are useful in treatment of inflammatory diseases. Such activities can be measured by the standard methods, for example, methods using experimental inflammatory disease model.

The compounds used in the present invention may be used as a medicine for animals and human beings and usually applied systemically or locally by the method of oral administration, intravenous injection (including instillation), subcutaneous injection, rectal administration and the like. While the dosage will vary depending on the animal or human patient, age, body weight, symptom to be treated, desired therapeutic effect, administration route, term of treatment and the like, satisfactory effects will be obtained with the dosage of 0.01–100 μg/eye administered locally (i.e. ocularly) or 0.001–500 mg/kg administered in 2 to 4 divided doses a day or as a sustained form.

As solid composition of this invention for oral administration, tablets, torches, buccals, capsule, pills, powders, granules and the like are included. The solid composition containing one or more active substances is mixed with at least an inactive diluent such as lactose, mannitol, glucose, hydoxypropyl cellulose, micro crystalline cellulose, starch, polyvinyl pyrolidone, magnesium aluminate metasilicate. The composition may contain additives other than the inactive diluent, such as lubricants e.g., magnesium stearate, a disintegrator e.g. cellulose calcium gluconates, stabilizers e.g. α, β- or γ-cyclodextrins, etherated cyclodextrins (e.g. dimethyl-α-, dimethyl-β-, trimethyl-β-, or hydroxypropyl-β-cyclodextrins), branched cyclodextrins (e.g. glucosyl- or maltosyl-cyclodextrins), formyl cyclodextrins, sulfur-containing cyclodextrins, misoprotols or phospholipids. Such cyclodextrins may form complex to increase the stability of the compounds. The stability may be often increased by forming lyposome with phospholipids. Tablets and pills may be coated with an enteric or gastroenteric film such as white sugar, gelatin, hydroxypropylcellulose, hydroxypropylmethylcellulose phthalates and the like, if necessary, and furthermore they may be covered with two or more layers. Additionally, the composition may be in the form of capsules made of substance easily absorbed such as gelatin. Further, when rapid effect is required, it may be in the form of buccal, in which glycerol, lactose etc are used as a base.

Liquid compositions for oral administration include pharmaceutically acceptable emulsions, solutions, suspensions, syrups, elixirs and the like and contain a generally used inactive diluent such as purified water or ethyl alcohol. The composition may contain additives such as wetting agents, suspending agents, sweeteners, flavors, perfumes and preservatives.

The compositions for oral administration may be sprays which contain one or more active substance and can be prepared according to a well known method.

The injection of this invention for non-oral administration includes serile aqueous or nonaqueous solutions, suspensions, and emulsions. Diluents for the aqueous solution or suspension include, for example, distilled water for injection, physiological saline and Ringer's solution. Diluents for the nonaqueous solution and suspension include, for example, propylene glycol, polyethylene glycol, vegetable oils such as olive oil, alcohols such as ethanol and polysorbates. The composition may contain other additives such as preservatives, wetting agents, emulsifying agents, dispersing agents and the like. These are sterilized by filtration through, e.g. a bacteria-retaining filter, compounding with a sterilizer, gas sterilization or radiation sterilization. These can also be prepared by producing a sterilized solid composition and dissolving in sterilized water or a sterilized solvent for injection before use.

Another formulation according to the present invention is the rectal or vaginal suppository. This can be prepared by mixing at least one active compound according to the invention with a suppository base which may be softened at body temperature, optionally containing non-ion surfactant having appropriate softening temperature for improving absorption.

A more complete understanding of the present invention can be obtained by reference to the following Preparation Examples, Formulation Examples and Test Examples which are provided herein for purpose of illustration only and are not intended to limit the scope of the invention.

PREPARATION EXAMPLE 1

Preparation of 16,16-difluoro-13,14-dihydro-15-keto-$PGE_1$ methyl ester (39)

1-1) Preparation of (1S,5R,6R,7R)-6-hydroxymethyl-7-tetrahydropyranyloxy-2-oxabicyclo[3.3.0]octan-3-one (29)

To a solution of commercial Corey lactone (THP-form, 37.9g) in tetrahydrofuran was added a solution (1.0 M, 300 ml) of tetrabutylammonium fluoride in tetrahydrofuran and resulting mixture was stirred at room temperature for 3 hours.

Then the reaction mixture was concentrated under reduced pressure and the residue was subjected to column chromatography to give the title compound (29).

Yield: 21.70 g (82.8%).

1-2) Preparation of (1S,5R,6R,7R)-6-{(E)-4,4-difluoro-5-oxo-2-octenyl}-7-tetrahydropyranyloxy-2-oxabicyclo[3.3.0]octan-3-one (31)

A solution (2.0 M, 45.5 ml) of oxalyl chloride in methylene chloride was diluted with methylene chloride under an argon atmosphere at −78° C. To this solution was added dropwise dimethylsulfoxide (12.9 ml) and the resulting mixture was stirred for 10 minutes. A solution (1S,5R,6R,7R)-6-hydroxymethyl-7-tetrahydropyranyloxy-2-oxabicylo[3.3.0]octan-3-one (29) (11.65 g) in methylene chloride was added dropwise and the mixture was stirred for 30 minutes. Then triethylamine (56 ml) was added dropwise and stirring was continued for further 1 hour. The reaction mixture was treated in the conventional manner to give the aldehyde (30) as a crude product.

To a solution of thallium ethoxide (3.26 ml) in methylene chloride was added under an argon atmosphere dimethyl 3,3-difluoro-2-oxoheptylphosphonate (11.9 g) and the resulting mixture was stirred for 1 hour. After cooling the solution to 0° C., a solution of the aldehyde (30) obtained above in methylene chloride was added dropwise to said solution and the mixture was stirred at room temperature for 14 hours. The reaction mixture was treated with acetic acid, celite and a saturated aqueous potassium idodide solution and filtered. The filtrate was treated in the conventional manner and the crude product was subjected to column chromatography to give the tile compound (31).

Yield: 7.787 g (44.3%).

1-3) Preparation of (1S,5R,6R,7R)-6-(4,4-difluoro-5-oxooctyl)-7-tetrahydropyranyloxy-2-oxabicyclo[3.3.0]octan-3-one (32)

To a solution of (1S,5R,6R,7R)-6-{(E)-4,4-difluoro-5-oxo-2-octenyl}-7-tetrahydropyranyloxy-2-oxabicyclo[3.3.0]octan-3-one (31) (5.57 g) in ethyl acetate was added 5% Pd/C (catalytic amount) and the resulting mixture was shaken under a hydrogen atmosphere at room temperature for 7 hours. The reaction mixture was filtered and the filtrate was concentrated under reduced pressure to give the tile compound (32) as a crude product. Yield: 5.48 g (97.8%).

1-4) Preparation of (1S,5R,6R,7R)-6-{4,4-difluoro-5(RS)-hydroxyoctyl}-7-tetrahydropyranyloxy-2-oxabicyclo-[3.3.0]-octan-3-one (33)

To a solution of (1S, 5R,6R,7R)-6-(4,4-difluoro-5-oxooctyl)-7-tetrahydropyranyloxy-2-oxabicyclo[3.3.0]octan-3-one (32) (5.48 g) in methanol was added sodium borohydride (0.800 g) at 0° C. and the resulting mixture was stirred for 10 minutes. The reaction mixture was treated in the conventional manner and the obtained crude product was subjected to column chromatography to give the title compound (33). Yield: 5.46 g (99.5%).

1-5) Preparation of 16,16-difluoro-13,14-dihydro-11-tetrahydropyranyloxy-PGF$_{2\alpha}$ methyl ester (36)

A solution of (1S,5R,6R,7R)-6-{4,4-dihydro-5(RS)hydroxyoctyl}-7-tetrahydropyranyloxy-2-oxabicyclo[3.3.0]-octan-3-one (33) (2.579 g) in toluene was cooled to −78° C. under an argon atmosphere. To this solution was added dropwise a solution (1.5 M, 9.6 ml) of diisobutylalmium hydride in toluene and stirred for 30 minutes. The reaction mixture was treated with methanol and a saturated aqueous Rochelle salt solution. Then the solution was treated in the conventional manner to give the lactol (34) as a crude product.

To a suspension of 4-carboxybutyl triphenyl phosphine bromide (11.72 g) in tetrahydrofuran was added dropwise under an argon atmosphere a solution (1.0 M, 52.84 ml) of potassium tert-butoxide in tetrahydrofuran and the resulting mixture was stirred for 20 minutes. The solution was cooled to 0° C. and combined with a solution of lactol (34) in tetrahydrofuran. The resulting mixture was stirred at room temperature for 15 hours and then treated in the conventional manner to give the carboxylic acid (35) as a crude product.

To a solution of the carboxylic acid (35) in acetonitrile was added under an argon atmosphere 1,8-diazabicyclo[5.4.0]undec-7-ene (DBU) (4.0 ml) and methyl iodide (1.7 ml) and the resulting solution was stirred at 60° C. for 30 hours. The solution was treated in the conventional manner and the product was subjected to column chromatography to give the title compound (36).

Yield: 2.737 g (84.5%).

1-6) Preparation of 16,16-difluoro-13,14-dihydro-15-keto-11-tetrahydropyranyloxy-PGE$_2$ methyl ester (37)

To a solution of Collins reagent, prepared from cromic anhydride (16.18 g) and pyridine (26.2 ml) in the conventional process, in methylene chloride was added a solution of 16,16-difluoro-13,14-dihydro-11-tetrahydropyranyloxy-PGF$_{2\alpha}$ methyl ester (36) (2,646 g) in methylene chloride under an argon atmosphere at −20° C. The resulting mixture was stirred at the same temperature for 2 hours and at −5° C. for 9 hours. The solution was treated with ether and sodium hydrogen sulfate and filtered. The filtrate was concentrated under reduced pressure and the residue was subjected to column chromatography to give the title compound (37). Yield: 1,890 g (64.4%).

1-7) Preparation of 16,16-difluoro-13,14-dihydro-15-keto-PGE$_2$ methyl ester (38)

Into a mixed solvent of acetic acid:water:tetrahydrofuran (3:1:1) was dissolved 16,16-difluoro-13,14-dihydro-15-keto-11-tetrahydroxypyranyloxy-PGE$_2$ methyl ester (37) (2.809 g) and the resulting solution was stirred at 60° C. for 5 hours. The reaction mixture was concentrated under reduced pressure and the residue was subjected to chromatography to give the title compound (38).

Yield: 1,755 g (75.5%).

1-8) Preparation of 16,16-difluoro-13,14-dihydro-15-keto-PGE$_1$ methyl ester (39)

To a solution of 16,16-difluoro-13,14-dihydro-15-keto-PGE$_2$ methyl ester (38) (1.755 g) in ethyl acetate was added Pd/C (catalytic amount) and the mixture was shaken under a hydrogen atmosphere at room temperature for 6 hours. The reaction mixture was filtered. The filtrate was concentrated and the residue was subjected to column chromatography to give the title compound (39).

Yield: 1. 655 g (93.8% ).

$^1$H NMR(CDCl$_3$) δ0.87(3H,t,J=7Hz), 1.15–2.05(23H,m), 2.11–2.30(3H,m), 2.50(1H,dd,J=7.5 and 17Hz), 3.10–3.20 (1H,br), 3.71(3H,s), 4.05–4.20(1H,m). MS(DI-EI) m/z 404(M+), 355 (M+—H$_2$O—CH$_3$O), 297(M+—C$_5$H$_9$F$_2$).

PREPARATION EXAMPLE 2

Preparation of 16,16-difluoro-13,14-dihydro-15-keto-PGE$_1$ (39')

2-1) Preparation of (15RS)-16,16-difluoro-13,14-dihydro-11-O-tetrahydropyranyl-PGF$_{2\alpha}$ benzyl ester (36)

To a solution of 16,16-difluoro-13,14-dihydro-11-O-tetrahydropyranyl-PGF$_{2\alpha}$ (35) (2.33 g) in dichloromethane (300 ml) were added DBU (2.1 ml) and benzyl bromide (2.2 ml) and the resulting mixture was stirred at room temperature for 1.5 hour. The reaction mixture was treated in the conventional manner and the crude product was purified by silica-gel column chromatography to give the title compound (36). Yield: 2.522 g (96.1%).

2-2) Preparation of 16,16-difluoro-13,14-dihydro-15-keto-11-O-tetrahydropyranyl-PGE$_2$ benzyl ester (37)

Collins reagent was prepared by using chromic anhydride (13.5 g) and pyridine (21.8 ml) in dichloromethane (300 ml), and to this were added Celite (40 g) and (15RS)-16,16-difluoro-13,14-dihydro-11-O-tetrahydropyranyl-PGF$_{2\alpha}$ benzyl ester (36) (2.550 g). The reaction mixture was treated in the conventional manner and the crude product was purified by silica-gel column chromatography to give the title compound (37). Yield: 1.991 g (78.6%).

2-3) Preparation of 16,16-difluoro-13,14-dihydro-15-keto-PGE$_2$ benzyl ester (38)

Into a mixed solvent of acetic acid:THF:water (3:1:1, 50 ml) was dissolved 16,16-difluoro-13,14-dihydro-15-keto-11-O-tetrahydropyranyl-PGE$_2$ benzyl ester (37)

(1.550 g) and the solution was kept at 50° C. for 4 hours. The reaction mixture was treated in the conventional manner and the crude product was purified by silica-gel column chromatography to give the title compound (38).

Yield: 1.225g (92.9%).

2-4) Preparation of 16,16-difluoro-13,14-dihydro-15-keto-PGE₁ (39')

To a solution of 16,16-difluoro-13,14-dihydro-15-keto-PGE₂benzyl ester (38) (0.844 g) in ethyl acetate (30 ml) was added 5% Pd/C and the mixture was shaken under a hydrogen atmosphere. The reaction mixture was treated in the conventional manner and the crude product was purified by silica-gel column chromatography to give the title compound (43). Yield: 0,404 g. $^1$H NMR(CDCl₃) δ0.94 (t,3H,J=7.5 Hz), 1.20–2.70 (m,26H), 4.19 (m,1H), 4.80 (br,2H). MS(DI-EI) m/z 390(M+), 372(M+—H₂O), 354(M+—2H₂O).

PREAPARATION EXAMPLE b 3

Preparation of 5(RS)-fluoro-13,14-dihydro-6,15-diketo-PGE₁ methyl ester [IUPAC nomenclature: 5(RS)-fluoro-7-{(1R,2s,3S)-3-hydroxy-2-(3-oxooctyl-5-oxocyclopentyl}-6-oxoheptanoate]

3-1) Preparation of (1S,5R,6R,7R)-6-[(E)-3-oxo-1-octenyl]-7-(4-phenyl)-benzoyloxy-2-oxabicyclo[3.3.0]octan-3-one (42)

Commercial (—)-Corey lactone (40) (10.0 g) in dichloromethane was subjected to Collins oxidation to give the aldehyde (41), which was reacted with an anion prepared from dimethyl (2-oxoheptyl)phosphonate (6.21 g). The reaction mixture was treated in the conventional manner and the obtained crude product was subjected to column chromatography to give the title compound (42).

Yield: 7.45g (60%).

3-2) Preparation of (1S,5R,6R,7R)-6-[(E)-3(RS)-hydroxy-1-octenyl]-7-(4phenyl)benzoyloxy-2-oxabicyclo[3.3.0]-octan-3-one (43)

To a solution of (1S,5R,6R,7R)-6-[(E)-3-oxo-1-octenyl]-7-(4-phenyl)benzoyloxy-2-oxabicyclo-[3.3.0]-octan-3-one (42) (7.45 g) in methanol were added cerium chloride (III) heptahydrate (6.84 g) at −20 ° C. and sodium borohydride (0.69 g) and the mixture was stirred for 1 hour.

The reaction mixture was treated in the conventional manner and the obtained crude product was subjected to the column chromatography to give the title compound (43) as a mixture of the diastereomers.

Yield: 7.64 g (theoretical).

3-3) Preparation of (1S,5R,6R,7R)-6-[(E)-3(RS)-t-butyl-dimethylsilyloxy-1-octenyl]-7-(4-phenyl)benzoyloxy-2-oxabicyclo[3.3.0]octan-3-one (44)

To a solution of (1S,5R,6R,7R)-6-[(E)-3(RS)hydroxy-1-octenyl]-7-(4-phenyl)benzoyloxy-2-oxabicyclo[3.3.0]octan-3-one (43) (7.65 g) in dimethyl formamide were added imidazol (2.27 g) and t-butyldimethylsilyl chloride (3.78 g) and the mixture was stirred for 1 hour.

The reaction mixture was treated in the conventional manner and the obtained crude product was subjected to the silica gel column chromatography to give the title compound (44) as a mixture of the diastereomers.

Yield: 7.49 g (80%).

3-4) Preparation of (1S,5R,6R,7R)-6-[(E)-3(RS)-t-butyldimethylsilyloxy-1-octenyl]-7-hydroxy-2-oxabicyclo]3.3.0]octan-3-one (45)

A mixture of (1S,5R,6R,7R)-6-[(E)-3(RS)-t-butyl-dimethylsilyloxy-1-octenyl]-7-(4-phenyl)benzoyloxy-2-oxabicyclo[3.3.0]octane-3-one (44) (7.49 g), potassium carbonate (1.10 g) and methanol was stirred at room temperature for 16 hours. The reaction mixture was treated in the conventional manner and the obtained crude product was subjected to the silica gel column chromatography to give the title compound (45) as a mixture of the diastereomers.

Yield: 4.69 g (92%).

3-5) Preparation of (1S,5R,6R,7R)-6-[(E)-3(RS)-t-butyldimethylsilyloxy-1-octenyl]-7-tetrahydropyranyloxy-2-oxabicyclo[3.3.-0]octan-3-one (46)

To a solution of (1S,5R,6R,7R)-6-[(E)-3(RS)-t-butyl-dimethylsilyloxy-1-octenyl]-7-hydroxy-2-oxabicy-clo[3.3.0]octan-3-one (45) (4.69 g) in methylene chloride were added dihydropyran (5.17 g), and pyridinium p-toluenesufonate (0.77 g), and the resultant mixture was stirred at room temperature for 16 hours. The reaction mixture was treated in the conventional manner and the obtained crude product was subjected to the silica gel column chromatography to give the title compound (46) as a mixture of the diastereomers.

Yield: 5.37 g (94%).

3-6) Preparation of methyl 2-{(1R,2R,3R,5S)-2-[(E)-3(RS)-t-butyldimethyl-silyloxy-1-octenyl]-5-hydroxytetrahydropyranyloxy-cyclopentyl}acetate (47)

To a solution of (1S,5R,6R,7R)-6-[(E)-3(RS)t-butyl-dimethylsilyloxy-1-octenyl]-7-tetrahydropyranyloxy-2-oxabicyclo[3.3.0]octan-3-one (46) (1.85 g) in a mixed solvent of methanol and water (4:1) was added lithium hydroxyde (0.33 g). The resultant mixture was stirred at room temperature for 16 hours. The reaction mixture was neutralized and extracted with ethyl acetate. Then, the organic layer was separated and an ether solution of diazomethane was added thereto. The resultant mixture was stirred at room temperature for 1 hour. The reaction mixture was treated in the conventional manner and the obtained crude product was subjected to the silica gel column chromatography to give the title compound (47) as a mixture of the diastereomers.

Yield: 1.82 g (92%).

3-7) Preparation of methyl 2-{(1R,2R,3R,5S)-2-[(E)-3(RS)-t-butyldimethylsilyloxy-1-octenyl]-3,5-bis-tetrahydropyranyl-oxy-cyclopentyl}acetate (48)

To a solution of methyl 2-{(1R,2R,3R,5S)-2[(E)-3(RS)-t-butyldimethylsilyloxy-1-octenyl]-5-hydroxytetrahydropyranyloxy-cyclopentyl}acetate (47)(4.45 g) in methylene chloride were added dihydropyran (3.75 g) and pyridinium p-toluenesufonate (0.56 g), and the resultant mixture was stirred at room temperature for 16 hours. The reaction mixture was treated in the conventional manner and the obtained crude product was subjected to the silica gel column chromatography to give the title compound (48) as a mixture of the diastereomers.

Yield: 4.24 g (74%).

3-8) Preparation of methyl 6-benzoyloxy-2(RS)-{2-[(1R,2R,3R,5S)-2-[(E)-3(RS)-t-butyldimethylsilyloxy-1-octenyl]-3,5-bis-tetrahydropyranyloxy-cyclopentyl]-1(RS)-hydroxyethyl}-2(SR)-fluorohexaneacetate (49)

To a toluene solution of methyl 2-{(1R,2R,3R,5S)-2-[(E)-3(RS)-t-butyldimethylsilyloxy-1-octenyl]-3,5-bis-tetrahydropyranyloxy-cyclopentyl}acetate (48) (0.5 g) was added a toluene solution of DIBAL-H (1.5 M, 1.43 ml) at −78° C. and the resultant mixture was stirred for 1 hour. The reaction mixture was treated in the conventional manner to give the aldehyde as a crude product.

The solution of LDA, prepared in the conventional manner, in terahydrofuran (0.94 mmol) was cooled to −78° C., and methyl 6-benzoyloxy-2(RS)-fluorohexanoate (f) (0.23 g) was added thereto. The resultant mixture was stirred for 10 minutes and the solution of the crude aldehyde in tetrahydrofran was added thereto. The reaction mixture was heated to room temperature and stirred at the same temperature for 1 hour, The crude product obtained in the conventional manner was subjected to the silica gel column chromatography to give the title compound (49) as a mixture of the diastereomers.

Yield: 0.51 g (74%).

3-9) Preparation of methyl 2(RS)-{2-[(1R,2R,3R,5S)-2-[(E)-3(RS)-t-butyldimethylsilyloxy-1-octenyl]-3,5-bistetrahydropyranyloxy-cyclopentyl]-1(RS)-hydroxyethyl}-2(SR)-fluoro-6-hydroxyhexanoate (50)

To a solution of methyl 6-benzoyloxy-2(RS)-{2-[(1R,2R,3R,5S)-2-[(E)-3(RS)-t-butyldimethylsilyloxy-1-octenyl]-3,5-bis-tetrahydropyranyloxy-cyclopentyl]-1(RS)hydroxyethyl-2(SR)-fluorohexaneacetate (49) (2.48 g) in methanol was added potassium carbonate (2.47 g) in methanol and the resultant mixture was stirred at room temperature for 24 hours. The crude product obtained in the conventional manner was subjected to the silica gel column chromatography to give the title compound (50).

Yield: 1.50 g (69%).

3-10) Preparation of 7-{(1R,2R,3R,5S)-2-[(E)-3(RS)-t-butyldimethylsilyloxy-1-octenyl]-3,5-bis-tetrahydropyranyloxocyclopentyl}-5(RS)-methoxycarbonyl-5(SR)-fluoro-6-oxoheptanoate (51)

Methyl 2(RS)-{2-[(1R,2R,3R,5S)-2-[(E)-3(RS)-t-butyldimethylsilyloxy-1-octenyl]-3,5-bis-tetrahydropyranyloxycyclopentyl]-1(RS)-hydroxyethyl}-2(SR)-fluoro-6-hydroxyhexanoate (50) (1.23g) was subjected to Collins oxidation at −50° C. under an argon atmosphere for 4.5 hours. The crude product obtained in the conventional manner was dissolved into ether, and a solution of diazomethane in ether was added thereto. The resultant mixture is stirred at room temperature for 1 hour. The reaction mixture was treated in the conventional manner and the obtained crude product was subjected to the silica gel column chromatography to give the title compound (51) in the form of diastereomeric mixture. Unreacted starting material (50) was recovered (0.41 g, Recovery: 33%).

Yield: 0.60g (47%).

3-11) Preparation of methyl 7-{(1R,2R,3R,5S)-2-[(E)-3(RS)-t-butyldimethylsilyloxy-1-octenyl]-3,5-bis-tetrahydropyranyloxycyclopentyl]-5(RS)-fluoro-6-oxo-heptanoate (52)

Methyl 7-{(1R,2R,3R,5S)-2-[(E)-3(RS)-t-butyldimethylsilyloxy-1-octenyl]-3,5-bis-tetrahydropyranyloxy cyclopentyl]-5(RS)-methoxycarbonyl-5(SR)-fluoro-6-oxoheptanoate (51) (0.80 g) was dissolved into a mixture of dimethyl sulfoxide, sodium chloride and water (50:2.8:1) and the resultant mixture was stirred at 135°–140° C. under an argon atmosphere for 1.5 hours. The crude product obtained by treating in the conventional manner was subjected to silica gel column chromatography to give the title compound (12) as a mixture of diastereomers.

Yield: 0.55 g (75%).

3-12) Preparation of methyl 5(RS)-fluoro-7-{(1R,2R,3R,5S)-2-[(E)-3(RS)-t-hydroxy-1-octenyl]-3,5-bis-tetrahydropyranyloxycyclopentyl]-6-oxoheptanoate (53)

To a solution of methyl 7-{(1R,2R,3R,5S)-2-[(E)-3(RS)-t-butyldimethylsilyloxy-1-octenyl]-3,5-bistetrahydropyranyloxy-cyclopentyl}-5(RS)-fluoro-6-oxoheptanoate (52) (0.52 g) in tetrahydrofuran was added a solution of tetra-n-butylammonium fluoride in tetrahydrofuran (1M, 23 ml), and the resultant mixture was stirred at room temperature for 40 hours. The crude product obtained by treating in the conventional manner was subjected to silica gel chromatography to give the title compound (53).

Yield: 0.34 g (67%).

3-13) Preparation of methyl 5(RS)-fluoro-7-{(1R,2R,3R,5S)-2-[3(RS)-hydroxy-1-octyl]-3,5-bistetra-hydropyranyloxycyclopentyl}-6-oxoheptanoate (54)

To a solution of methyl 5(RS)-fluoro-7-{(1R,2R,3R,5S)-2-[(E)-3(RS)-t-hydroxy-1-octenyl]-3,5-bistetrahydropyranyloxycyclopentyl}-6-oxoheptanoate (53) in ethyl acetate was added 5% of Pd/C (0.06 g), and the resultant mixture was stirred at room temperature under a hydrogen atmosphere for 16 hours. The reaction mixture was treated in the conventional manner and the obtained crude product was subjected to silica gel column chromatography to give the title compound (54) as a mixture of diastereomers.

Yield: 0.30 g (88%).

3-14) Preparation of methyl 5(RS)-fluoro-7-{(1R,2R,3R,5S)-2-[3-oxo-octyl]-3,5-bis-tetrahydropyranyloxy-cyclopentyl}-6-oxoheptanoate (55)

To a solution of methyl 5(RS)-fluoro-6-oxo-7{(1R,2R,3R,5S)-2-[3(RS)-hydroxy-1-octyl]-3,5-bis-tetrahydropyranyloxy-cyclopentyl}-6-oxo-heptanoate (54) (0.30 g) in acetone was added Jones reagent (2.60M, 0.6 ml) and the resultant mixture was stirred at −30° C. for 1.5 hours. The reaction mixture was treated in the conventional manner and the obtained crude product was subjected to silica gel column chromatography to give the title compound (55) as a mixture of diastereomers.

Yield: 0.24 g (80%).

3-15) Preparation of methyl 5(RS)-fluoro-7-{(1R, 2R, 3R)-3-t-butyldimethylsilyloxy-5-oxo-2-(3-oxo-octyl)cyclopentyl}-6-oxoheptanoate (57)

Methyl 5(RS)-fluoro-6-oxo-7-{(1R,2R,3R,5S)-2-[3-oxo-octyl]-3,5-bis-tetra-hydropyranyloxy-cyclopentyl}-6-oxo-heptanoate (55) (0.24 g) was dissolved into a mixed solvent of acetic acid, tetrahydrofuran and water (3:1:1), and the resultant mixture was stirred at 45° C. for 4.5 hours. The crude product obtained by treating in the conventional manner was subjected to silica gel column chromatography to give a diol product (56) (0.15 g).

To a solution of diol product (56) (0.15 g) in dimethylformamide were added imidazol (0.35 g) and t-butyldimethylsilyl chloride (0.38 g) and the resultant mixture was stirred at room temperature for 5 hours. The crude product obtained by treating in the conventional manner was subjected to silica gel column chromatography to give monosilyl product (0.135 g).

The monosilyl product (0.135 g) was subjected to Collins oxidation in methylene chloride at room temperature for 15 minutes. The crude product obtained by treating in the conventional manner was subjected to silica gel column chromatography to give the title compound (57).

Yield: 0.10 g (49%, starting from Compound (55)).

3-16) Preparation of 5(RS)-fluoro-13,14,-dihydro-6,15-diketo-PGE$_1$ methyl ester (58)

To a solution of methyl 5(RS)-fluoro-7-{(1R,2R,3R)-3-t-butyldimethylsilyloxy-5-oxo-2-(3-oxooctyl)-cyclopentyl}-6-oxoheptanoate (57) (0.05 g) in dichloromethane was added a solution of hydrogen fluoride-pyridine (70:30, 0.40 ml), and the resultant mixture was stirred at room temperature for 7 hours. The crude product obtained by treating in the conventional manner was subjected to silica gel column chromatography to give the title compound (58).

Yield: 0.38 g (98%).

$^1$H NMR (CDCl$_3$): δ 0.87(3H,t,J=6.8Hz), 1.16–2.05(14H,m), 2.23–3.15(11H,m), 3.66(3H,s), 3.98–4.12(1H,m), 4.62–4.70(0.5H,m), 4.85–4.95(0.5H,m).

Preparation of Starting Material: Methyl 6-benzoyloxy-2(RS)-fluoro-hexanoate (f)

1) Preparation of benzyl 6-hydroxyhexanoate (b)

A mixture of ε-caprolactone (a) (40 g), benzyl alcohol and p-toluenesulfonic acid monohydrate (0.7 g) was stirred at 100° C. for 16 hours. The reaction mixture was treated in the conventional manner and was distilled under reduced pressure (1 mmHg, 140°–154° C.) to give the title compound (b).

Yield: 27.37 g (35%).

2) Preparation of benzyl 6-benzoyloxyhexanoate (c)

To a solution of benzyl 6-hydroxyhexanoate (b) (27.37 g) in methylene chloride were added 4-dimethyl amino pyridine (19.5 g) and benzoyl chloride (19.53 g), and the resultant mixture was stirred for 2 hours. The reaction mixture was treated in the conventional manner and was distilled under reduced pressure (1 mmHg, 190°–215° C.) to give the title compound (c).

Yield: 38.09 g (95%).

3) Preparation of 6-benzoyloxy-hexanoic acid (d)

To a solution of benzyl 6-benzoyloxy-hexanoate (c) (38.09 g) in ethyl acetate was added 5% Pd/C (3 g) and the resultant mixture was stirred under a hydrogen atmosphere for 24 hours. The crude product obtained by treating in the conventional manner was distilled under reduced pressure (1 mmHg, 182°–192° C.) to give the title compound (d).

Yield: 4.92 g (90%).

4) Preparation of methyl 6-benzoyloxy-2(RS)-bromohexanoate (e)

Thionyl chloride (22 ml) was added dropwise to 6-benzoyloxyhexanoic acid (d) (14.92 g), and the resultant mixture was stirred at 65° C. for 1 hour. To the reaction mixture were added carbon tetrachloride (50 ml), N-bromosuccinimide (22.5 g) and 48% hydrobromic acid (5 drops), and the resultant mixture was stirred at 85° C. for 20 hours. The reaction mixture was allowed to cool, and was filtered to remove solid product. The filtrate was concentrated under reduced pressure. The obtained residue was dissolved into methanol and the resultant mixture was stirred at room temperature. The crude product obtained by treating in the conventional manner was subjected to silica gel chromatography to give the title compound (e).

Yield: 14.02 g (67%).

5) Preparation of methyl 6-benzoyloxy-2(RS)-fluorohexanoate (f)

A mixture of methyl 6-benzoyloxy-2(RS)-bromohexanoate (e) (14.02 g), potassium fluoride (12.59 g) and acetamide (12.3 g) was stirred at 105° C. for 6 hours. The crude product obtained by treating in the conventional manner was subjected to silica gel chromatography to give the title compound (f) and methyl 6-benzoyloxyhexanoate (g) (3.11 g, yield: 29%).

Yield: 5.28 g (46%).

$^1$H NMR (CDCl$_3$)δ: 1.55–2.18 (6H,m), 3.79(3H,s), 4.33(2H,t,J=7Hz), 4.77–4.86(0.5H,m), 5.05–5.12(0.5H,m), 7.40–7.62(3H,m), 8.00–8.10(2H,m).

PREPARATION EXAMPLE 4

Preparation of 5,5-difluoro-13,14-dihydro-6,15-diketo-PGE$_1$ methyl ester (72)

4-1) Preparation of (1S,5R,6R,7R)-6-[(E)-3-oxo1-octenyl]-7-(4-phenylbenxoyloxy)-2-oxabicyclo[3.3.0]-octan-3-one (42)

Corey-lactone (40) (10.0 g) dissolved in dichloromethane (160 ml) was subjected to Moffatt oxidation using DMSO (79.2 g), dicyclohexylcarbodiimide (24.0 g), pyridine (2.3 ml) and trifluoroacetic acid (1.1 ml) to give Corey-lactone aldehyde (2a). Separately, dimethyl (2-oxoheptyl)phosphonate anion was prepared from dimethyl-(2-oxoheptyl)phosphonate (6.31 g) and sodium hydride (60%, 0.13 g) in dichloromethane, and the solution of the previously obtained aldehyde (160 ml) was added dropwise thereto, and the resultant mixture was stirred at room temperature for 11.5 hours. The crude product obtained by treating in the conventional manner was subjected to silica gel chromatography to give the title compound (42).

Yield: 10.8 g (85.3%).

4-2) Preparation of (1S,5R,6R,7R)-6-(3-oxo-1-octenyl)-7-(4-phenylbenzoyloxy)-2-oxabicyclo[3.3.0]octan-3-one (4a)

A mixture of (1S,5R,6R,7R)-6-[(E)-3-oxo-1-octenyl]-7-(4-phenylbenzoyloxy)-2-oxabicycloctan[3.3.0]3-one (42) (10.8 g) and 5% Pd/C (1.02 g) in e (150 ml) was stirred under a hydrogen atmosphere for 3 hours. The reaction mixture was treated in the conventional manner to give the title compound (4a).
Yield: 8.20 g.

4-3) Preparation of (1S,5R,6R,7R)-6-(3,3-ethylenedioxyoctyl-7-(4-phenylbenzoyloxy)-2-oxabicyclo[3.3.0]-octan-3-one (5)

To a solution of (1S,5R,6R,7R)-6-(3-oxo-1-octenyl)-7-(4-phenylbenzoyloxy)-2-oxabicyclo[3.3.0]octan-3-one (4a) (8.20 g) in toluene (100 ml) were added ethylene glycol (23.0 g) and p-toluenesulfonic acid (0.41 g), and the resultant mixture was refluxed for 4 hours. Water formed in the reaction was removed by azeotropic distillation. The reaction mixture was treated in the conventional manner and was subjected to silica gel column chromatography to give the title compound (5a).
Yield: 8.23 g (91.3%).

4-4) Preparation of (1S,5R,6R,7R)-6-(3,3-ethylenedioxyoctyl)-7-hydroxy-2-oxabicyclo[3.3.0]octan-3-one (6a)

To a solution of (1S,5R,6R,7R)-6-(3,3-ethylenedioxyoctyl-7-(4-phenylbenzoyloxy)-2-oxabicyclo[3.3.0]octan-3-one (5a) (8.20 g) in methanol (200 ml) was added potassium carbonate (1.15 g) and the resultant mixture was stirred overnight, and acetic acid (1 ml) was added thereto. The crude product obtained by treating in the conventional manner was subjected to silica gel column chromatography to give the title compound (6a).
Yield: 4.70 g (90.0%).

4-5) Preparation of (1S,5R,6R,7R)-6-(3,3-ethylenedioxyoctyl)-7-tetrahydropyranyloxy-2-oxabicyclo[3.3.0]octan-3-one (59)

A solution of (1S,5R,6R,7R)-6-(3,3-ethylenedioxyoctyl)-7-hydroxy-2-oxabicyclo[3.3.0]octan-3-one (6a) (4.70 g) in dichloromethane (200 ml) was cooled on ice and dihydropyran (2.41 g) and p-toluenesulfonic acid (0.23 g) were added thereto and the resultant mixture was stirred for 1.5 hours. The crude product obtained by treating in the conventional manner was subjected to silica gel column chromatography to give the title compound (59).
Yield: 5.54 g (93%).

4-6) Preparation of methyl 2-[(1S,2R,3R,5S)-2-(3,3-ethylenedioxyoctyl)-3-(tetrahydropyranyloxy)-5-hydroxycyclopentyl]acetate (61)

(1S,5R,6R,7R)-6-(3,3-ethylenedioxyoctyl)-7-tetrahydropyranyloxy-2-oxabicyclo[3.3.0]octan-3-one (59) (5.54 g) was dissolved into methanol (61 ml), and 5% aqueous potassium hydroxyde (37 ml) was added thereto. The resultant mixture was stirred at 50° C. for 30 minutes. While cooling on ice, the reaction mixture was neutralized with aqueous 0.5N hydrochloric acid and the acid (60) obtained by treating in the conventional manner was treated with diazomethane to give the title compound (61).
Yield: 5.74 g.

4-7) Preparation of methyl 2-[(1S,2R,3R,5S)-2-(3,3-ethylene dioxyoctyl)-3-(tetrahydropyranyloxy)-5-(t-butylsilyloxy)-cyclopentyl]acetate (62)

To a solution of methyl 2-[(1S,2R,3R,5S)-2-(3,3-ethylenedioxyoctyl)-3-(tetrahydropyranyloxy)-5-hydroxycyclopentyl]acetate (61) in DMF (80 ml) were added t-butyldimethylsilyl chloride (2.11 g) and imidazol (0.95 g), and the resultant mixture was stirred. The crude product obtained by treating in the conventional manner was subjected to silica gel column chromatography to give the title compound (62).
Yield: 5.41 g (71.2 g).

4-8) Preparation of 2-[(1S,2R,3R,5S)-2-(3,3-ethylenedioxyoctyl)-3-(tetrahydropyranyloxy)-5-(t-butyldimethylsilyloxy)cyclopentyl]ethanol (63)

Methyl 2-[(1S,5R,6R,7R)-2-(3,3-ethylenedioxyoctyl)-3-(tetrahydropyranyloxy)-5-(t-butyldimethylsiloxy)cyclopentyl]acetate (62) was reduced with lithium aluminium hydride in ether (150 ml). The crude product obtained by treating in the conventional manner was subjected to silica gel column chromatography to give the title compound (63).
Yield: 4.81 g (93.8%).

4-9) Preparation of 2-[(1S,5R,6R,7R)-2-(3,3-ethylenedioxyoctyl)-3-(tetrahydropyranyloxy)-5-(t-butyldimethylsilyloxy)cyclopentyl]acetaldehyde (64)

A solution of 2-[(1S,5R,6R,7R)-2(3,3-ethylenedioxyoctyl)- 3-(tetrahydropyranyloxy)-5-(t-butylsiloxy) cyclopentyl]ethanol (63) in dichloromethane (50 ml) was subjected to Swan oxidation using oxalyl chloride (1.78 g), DMSO (2.19 g) and triethylamine (4.37 g) to give the title compound (12).
Yield: 4.60 g (96.0%).

4-10) Preparation of 1-[(1R,2R,4S,5R)-2-tetrahydropyranyloxy-4-t-butylsilyloxy-5-{2(RS)-hydroxy-3,3-difluoro-7-t-butyldimethylsilyloxy-4-heptynyl}-cyclopentyl]-3,3-ethylenedioxy-octane (65)

To a solution of 2-[(1S,2R,3R,5S)-2-(3,3-ethylenedioxyoctyl)-3-(tetrahydropyranyloxy)-5-(t-butylsiloxy)-cyclopentyl]acetaldehyde (64) (1.00 g) in THF (25 ml) was added activated zinc powder (2.54 g), and while cooling on ice, the solution of 1-bromo-1,1-difluoro-5-(t-butyl-dimethylsilyloxy)-2-pentyne (i) (0.92 g) in THF (5 ml) was added dropwise to the resultant mixture. To the resultant solution was. added mercury chloride (0.11 g) and the resultant mixture was stirred under ultrasonic irradiation. The reaction mixture was treated in the conventional manner and the obtained crude product was subjected to silica gel column chromatography to give the title compound (65).
Yield: 1.40 g (95.9%).

4-11) Preparation of 1-[(1R,2R,4S,5R)-2-tetrahydropyranyloxy-4-hydroxy-5-{2(RS),7-dihydroxy-3,3-difluoro-4-heptyl}cyclopentyl]-3,3-ethylenedioxyoctane (67)

A solution of 1-[(1R,2R,4S,5R)-2-tetrahydropyranyloxy-4-t-butylsilyloxy-5-{2(RS)-hydroxy-3,3-difluoro-7-t-butyldimethylsilyloxy-4-heptynyl}cyclopentyl]-3,3-ethylenedioxy-octane (65) (0.96 g) in THF (15 ml) was cooled on ice and tetrabutyl ammonium fluoride (1M, 0.57 ml) was added thereto and the resultant mixture was stirred for 12 hours. The reaction mixture was treated in the conventional manner and the obtained crude product was subjected to silica gel chromatography to give the triol (66) (0.492 g).

The triol (66) was subjected to catalytic hydrogenation over 5% Pd/C (0.06 g) in ethyl acetate (50 ml). The reaction mixture was treated in the conventional manner and the obtained crude product was subjected to silica gel chromatography to give the title compound (67).

Yield: 0.487 g (98.6%).

4-12) Preparation of 5,5-difluoro-6-keto-11-pyranyloxy-15,15-ethylenedioxy-13,14-dihydro-PGE$_1$ methyl ester (70)

A solution of 1-[(1R,2R,4S,5R)-2-tetrahydropyranyloxy-4-hydroxy-5-{2(RS),7-dihydroxy-3,3-difluoro-4-heptynyl}cyclopentyl]-3,3-ethylenedioxyoctane (67) (0.487 g) in dichloromethane (18 ml) was subjected to Swan oxidation using oxalyl chloride (1.17 g), DMSO (1.51 g) and triethylamine (3.1 g) to give the diketoaldehyde (68) (0.321 g, Y: 67.3%).

The obtained diketoaldehyde (68) (0.212 g) was subjected to Jones oxidation using Jones reagent (2.67M 153.6μ) at a temperature between −50° C. and −40° C. to give the carboxylic acid (69), which was reacted with diazomethane in order to obtain methyl ester. The obtained crude product was subjected to silica gel column chromatography to give the title compound (70).

Yield: 0.152 g (67.8%).

4-13) Preparation of 5,5-difluoro-13,14-diketo-PGE$_1$ methyl ester (72)

A solution of 5,5-difluoro-6-keto-11-pyranyloxy-13,14-dihydro-15,15-ethylenedioxy-PGE$_1$ methyl ester (70) (0.152 g) in a mixed solvent of acetic acid/THF/water (2/1/1) (6 ml) was kept at 45°–50° for 2.5 hours. The reaction mixture was treated in conventional manner and the obtained crude product was subjected to silica gel column chromatography to give. the title compound (72).

Yield: 0.101 g (87.0%).

* 13,14-dihydro-6,15-diketo-5,5-difluoro-PGE$_1$ methyl ester.

$^1$NMR (CDCl$_3$) δ0.88(t,3H,J=6.6 Hz), 1.10–1.40(m,4H), 1.45–2.20(m,10H), 2.20–3.15(m, 11H), 3.67(s,3H), 4.00–4.18 (m,1H).

MS(DI/EI) m/z 418(M+), 400(M+−H$_2$O), 360(M+−HF−H$_2$O), 99(C$_6$H$_{11}$CO+).

Preparation of Starting Material:5-(t-butyldimethylsiloxy)-1-bromo-1,1-difluoro-3-pentyne (i)

1) Preparation of 5-(t-butyldimethylsiloxy)-3-pentyne (h)

To a solution of 3-butyn-1-ol (g) (10.0 g) in DMF (80 ml) were added t-butyldimethylsilyl chloride (21.5 g) and imidazol (10.6 g), and the resultant mixture was kept at 35° C. for 7 hours. The reaction mixture was treated in the conventional manner and the obtained crude product was distilled to give the title compound (h).

Yield: 17.4 g (66%).

2) Preparation of 5-(t-butyl-dimethylsiloxy-1-bromo-1,1-difluoro-3-pentyne) (i)

A solution of 5-(t-butyldimethylsiloxy)-3-pentyne (h) (8.00 g) in THF (100 ml) was cooled to −20° C. and n-butyl lithium (1.6M, 27.1 ml) was added dropwise thereto. The resultant mixture was stood at 0° C. and a solution of dibromodifluoromethane in THF (5 ml) was added, and the mixture was stirred for 2 hours. The reaction mixture was treated in the conventional manner and the obtained crude product was subjected to silica gel column chromatography to give the title compound (i).

Yield: 3.67 g (27%).

PREPARATION EXAMPLE 5

Preparation of 20-ethyl-2-decarboxy-2-(2-carboxyethyl)-13,14-dihydro-15-keto-PGF$_{2\alpha}$ isopropyl ester (76) [IUPAC nomenclature: isopropyl (Z)-9-(1R)-[(2R,3R,5S)-3,5-dihydroxy-2-(3-oxodecyl)-cyclopentyl]-7-nonenoate]

5-1) Preparation of (Z)-9-(1R)-[(2R,3R,5S)-2-(3,3-ethylenedioxydecyl)-5-hydroxy-3-(tetrahydropyranyloxy)cyclopentyl]-7-nonenoic acid (74)

Sodium hydride (60%, 0.422 g) was washed with hexane under an argon atmosphere. To this was added dimethyl sulfoxide (DMSO, 10 ml) and the resultant mixture was kept at 60° C. for 3 hours. After cooling to the room temperature, the resultant mixture was treated with 6-carboxyhexyltriphenylphosphonium bromide (2.49 g), stirred at the room temperature for 2 hours, then at 45° C. for 1 hour, and poured into ice-water. The resultant mixture was worked up with the conventional procedure to give the titled compound (74). Yield: 1.68 g.

5-2) Preparation of isopropyl (Z)-9-(1R)-[(2R,3R,5S)-2-(3,3-ethylenedioxydecyl)-5-hydroxy-3-(tetrahydropyranyloxy)cyclopentyl]-7-nonenoate (75)

The compound (74) (1.68 g) was esterified in the conventional procedure with 1,8-diazabicyclo[5.4.0]-7-undecene (DBU, 0.78 ml) and isopropyl iodide (0.35 ml) in acetonitrile (15 ml). The residue was subjected to silicagel column chromatography to give the titled compound (75). Yield: 0.908 g (88%).

5-3) Preparation of isopropyl (Z)-9-(1R)-[(2R,3R,5S)-3,5-dihydroxy-2-(3-oxodecyl)cyclopentyl]-7-nonenoate (76)

The compound (75) (0.305 g) was dissolved in a mixed solvent (6 ml) consisting of acetic acid, THF and water (2:1:1) and kept at 50° C. for 14 hours. The resultant mixture was worked up with the conventional procedure and the obtained crude product was subjected to silicagel column chromatography to give the titled compound (76). Yield: 0.213 g (90%).

Compound (76) [Q$_1'$=Q$_2'$=H, Rb'−Rc'=hexyl, P$_3$=isopropyl].

NMR(CDCl$_3$)δ: 0.85 (t,3H,J=6.5Hz), 1.20 (d,6H,J=6Hz), 1.23–2.65 (m,34H), 3.86 (m,1H), 4.16 (m.1H), 4.99 (Hept,1H,J=6Hz), 5.39 (m,2H)

PREPARATION EXAMPLE 6

Preparation of 20-ethyl-2-decarboxy-2-(2-carboxyethyl-13,14-dihydro-15-keto-PGE₂ isopropyl ester (46) [IUPAC nomenclature: isopropyl (Z)-9-(1R)-[(2R,3R)-3-hydroxy-5-oxo-2-(3-oxodecyl)-cyclopentyl]-7-nonenoate]

6-1) Preparation of (Z)-9-(1R)-[(2R,3R)-2-(3,3-ethylenedioxydecyl)-5-oxo-3-(tetrahydropyranyloxy)cyclopentyl]-7-nonenoate (77)

Oxalyl chloride (2M, 0.45 ml) and DMSO (0.13 ml) were added to dichloromethane (5 ml) cooled previously to −70° C. and the resultant mixture was stirred for 15 hours. A solution of isopropyl (Z)-9-(1R)-[(2R,3R,5S)-2-(3,3-ethylenedioxydecyl)-5-hydroxy-(3-tetrahydropyranyloxy)cyclopentyl]- 7-nonenoate (75) (0.35 g) in dichloromethane (7 ml) was added dropwise to the above solution. After stirring at −55° C. for 15 minutes, the resultant mixture was treated with triethylamine (0.25 ml) and warmed up to 10° C. over 6 hours. The resultant mixture was worked up with the conventional procedure and the obtained crude product was subjected to silicagel column chromatography to give the titled compound (77). Yield: 0.311 g (89%).

6-2) Preparation of isopropyl (Z)-9-(1R)-[(2R,3R)-3-hydroxy-5-oxo-2-(3-oxodecyl)-cyclopentyl]-7-nonenoate (78)

The compound (77) (0.311 g) was dissolved in a mixed solvent (5 ml) consisting of acetic acid, THF and water (2:1:1) and kept at 50° C. for 3 hours. The resultant mixture was worked up with the conventional procedure and the residue was subjected to silicagel column chromatography to give the titled compound (78). Yield: 0.156 g (66%).

Compound (46) [$Q_1'=Q_2'=H$ $Rb'-Rc'=hexyl$, $P_3=$isopropyl].

NMR(CDCl₃)δ:0.86 (t,3H,J=6.5Hz), 1.20 (d,6H,J=6Hz), 1.23–2.75 (m,33H), 4.20 (m,1H), 4.99 (Hept,1H,J=6Hz), 5.15–5.50 (m,2H)

PREPARTION EXAMPLE 7

Preparation of 2-decarboxy-2-(2-carboxyethyl)-13,14-dihydro-16,16-difluoro-15-keto-PGE₂ (79) [IUPAC nomenclature: (Z)-9-(1R)-[(2R,3R)-2-(4,4-difluoro-3-oxo-octyl)-3-hydroxy-5-oxopentyl]-7-nonenoic acid]

Preparation of starting compound: (6-carboxyhexyl)-triphenylphosphonium bromide (n).

A mixture of 7-bromoheptanonitrile (l) (10.0 g) and 40% hydrobromic acid (80 ml) was heated under reflux for 6 hours. The mixture was diluted with water, extracted with ether and then worked up with the conventional procedure to give a crude product. The residue was subjected to silicagel column chromatography to give 7-bromoheptanoic acid (n). Yield: 7.60 g (69%).

Treatment of 7-bromoheptanoic acid (n) (7.60 g) with triphenylphosphine (10.0 g) gave (6-carboxyhexyl)triphenylphosphonium bromide (n). Yield: 16.0 g (93%).

PREPARATION OF THE DESIRED COMPOUND

7-1) Preparation of (1S,5R,6R,7R)-6-(4,4-difluoro-3-oxooctenyl)-7-(tetrahydropyranyloxy)-2-oxabicyclo[3.3.0]octan-3-one (82)

The Swern oxidation of (1S,5R,6R,7R)-6-hydroxymethyl-7-(tetrahydropyranyloxy)-2-oxabicyclo[3.3.-0]octan-3-one (48) (27.8 g), which was obtained from commercial (1S,5R,6R,7R)-6-(5-butyldimethylsilyloxymethyl)-7-(tetrahydropyranyloxy)-2-oxabicyclo[3.3.-0]octan-3-one (79), using oxalyl chloride (2.0M, 109.3 ml), DMSO (31.0 ml) and trimethylamine (150 ml) in dichloromethane (800 ml) gave the compound (81) ($P_1=$tetrahydropyranyl).

The above compound (81) was reacted with dimethyl 3,3-difluoro-2-oxoheptylphosphonate (30.0 g) in dichloromethane in the presence of thallium methoxide (8.23 ml). The resultant mixture was worked up with the conventional procedure and the obtained crude product was subjected to silicagel column chromatography to give the titled compound (82). Yield: 24.4 g (58%).

7-2) Preparation of (1S,5R,6R,7R)-6-(4,4-difluoro-3-oxooctyl)-7-tetrahydropyranyloxy-2-oxabicyclo[3.3.0]octan-3-one (83)

The compound (82) (12.7 g) was catalytically hydrogenated over 5% palladium on carbon (catalytic amount) in ethyl acetate (300 ml) under hydrogen atmosphere to give the titled compound (83). Yield: 12.5 g (99%).

7-3) Preparation of (1S,5R,6R,7R)-6-[4,4-difluoro-3(R,S)hydroxyoctyl]-7-tetrahydroxypyranyloxy)-2-oxabicyclo[3.3.0]octan-3-one (84)

The compound (83) (12.6 g) was reduced with sodium borohydride (1.25 g) in methanol (400 ml) at 0° C. to give the titled compound (84). Yield: 12.1 g (95.5%).

7-4) Preparation of (1S,5R,6R,7R)-6-[4,4-difluoro-3(R,S)hydroxyoctyl]-7-tetrahydroxypyranyloxy)-2-oxabicyclo[3.3.0]octan-3(R,S)-ol (85)

The compound (84) (12.1 g) was reduced with diisobutylaluminum hydride (1.5M, 65.1 ml) in toluene (500 ml) at −78° C. and the obtained crude product was subjected to silicagel column chromatography to give the titled compound (85). Yield: 11.1 g (91%).

7-5) Preparation of phenacyl (Z)-9-(1R)-[(2R,3R,5S)-2-{4,4-difluoro-(3RS)-hydroxyoctyl}-5-hydroxy-3-(tetrahydropyranyloxy)cyclopentyl]-7-nonenoate (87)

Sodium hydride (60%, 1.63 g) was washed with pentane. To this was added DMSO (40 ml) and the resultant mixture was kept at 65°–70° C. for 1.5 hours. After cooling to the room temperature, carboxyhexylphosphonium bromide (n) (9.61 g) was added to the mixture to form a ylid. A solution of the compound (85) in DMSO (15 ml) was added dropwise to the ylid in solution and the mixture was kept overnight at the room temperature. The resultant mixture was worked up with conventional procedure to give the compound (86). Yield: 3.18 g (crude).

The compound (86) (0.795 g), phenacyl bromide (1.01 g) and diisopropylethylamine (0.89 ml) were dissolved in acetonitrile (10 ml) and the solution was kept at the room temperature for 20 minutes and then at 45° C. for 30 minutes. The resultant mixture was worked up with the conventional procedure and the obtained crude product was subjected to silicagel column chromatography to give the titled compound (87). Yield: 0.604 g.

7-6) Preparation of phenacyl (Z)-9-(1R)-[(2R,3R)-2-{4,4-difluoro-3-oxooctyl}-5-oxo-3-(tetrahydropyranyloxy)cyclopentyl]- 7-nonenoate (88)

DMSO (0.92 ml) was added dropwise to a solution, cooled to −78° C., of oxalyl chloride 0.52 ml) in dichloromethane (30 ml). The compound (87) (0.609 g) dissolved in dichloromethane (15 ml) was added to the above solution and the resultant mixture was stirred at −30° C. to −20° C. for 1.5 hours. The resultant mixture was treated with triethylamine (1.88 ml) and stirred for 30 minutes. The resultant mixture was worked up with the conventional procedure and the obtained crude product was subjected to silicagel column chromatography to give the titled compound (88). Yield: 0.514 g (85%).

7-7) Preparation of phenacyl (Z)-9-(1R)-[(2R,3R)-2-{4,4-difluoro-3-oxooctyl}-3-hydroxy-5-oxocyclopentyl]-7-nonenoate (78)

The compound (88) (0.514 g) was dissolved in a mixed solvent (30 ml) consisting of acetic acid, THF and water (4:2:1) and the solution was kept overnight at the room temperature. The resultant mixture was worked up with the conventional procedure and the obtained crude product was subjected to silicagel column chromatography to give the titled compound (78). Yield: 0.272 g (61%).

Compound (78) [$Q_1'=Q_2'=F$, $Rb'-Rc'=butyl$, $P_3=phenacyl$].

NMR(CDCl$_3$)δ: 0.92 (t,3H,J=7.5Hz), 1.2–2.9 (m,27H), 4.18 (m,1H), 5.4 (m,2H), 7.4–8.0 (m,5H).

7-8) Preparation of (Z)-9-(1R)-[(2R,3R)-2-(4,4-difluoro-3-oxooctyl)-3-hydroxy-5-oxocyclopentyl]-7-nonenoic acid (89)

A solution of the compound (78) (0.272 g) in acetic acid (10 ml) was treated with zinc (3.5 g) added in portions at the room temperature for 2.5 hours. The resultant mixture was worked up with the conventional procedure and the residue was subjected to silicagel column chromatography to give the titled compound (89). Yield: 0.177 g (81%).

Compound (89) [$Q_1'=Q_2'=F$, $Rb'-Rc'=butyl$]
NMR(CDCl$_3$)δ: 0.93(t,3H,J=6.5Hz), 1.15–2.95 (m,28H), 4.19 (m,1H), 5.36 (m,1H)

PREPARATION EXAMPLE 8

Preparation of 2-decarboxy-2-(2-carboxyethyl)-13,14-dihydro-16,16-difluoro-15-keto-PGE$_1$ isopropyl ester [IUPAC nomenclature: isopropyl 9-(1R)-[(2R,3R)-2-(4,4-difluoro-3-oxooctyl)-3-hydroxy-5-oxocyclopentyl]nonanoate

8-1) Preparation of isopropyl (Z)-9-(1R)-[(2R,3R,5S)-2-{4,4-difluoro-(3RS)-hydroxyoctyl}-5-hydroxy-3-(tetrahydropyranyloxy)cyclopentyl]-7-nonenoate (87)

The compound (86) (0.802 g) obtained in Preparation Example 5, DBU (0.76 ml) and isopropyl iodide (0.51 ml) were dissolved in acetonitrile (15 ml) and kept at 50° C. for 1 hour. Further the compound (86) (0.492 g) was treated in the same way. The resultant mixture was worked up with the conventional procedure to give the titled compound (87). Yield (combined).: 0.315 g.

8-2) Preparation of isopropyl 9-(1R)-[(2R,3R)-2-{4,4-difluoro-(3RS)-hydroxyoctyl}-5-hydroxy-3-(tetrahydropyranyloxy)cyclopentyl]-7-nonanoate (90)

The compound (87) (0.315 g) was catalytically hydrogenated over palladium on carbon (5%, 0.08 g) in ethanol (20 ml) under hydrogen atmosphere to give the titled compound (90). Yield: 0.301 g (95%)

8-3) Preparation of isopropyl 9-(1R)-[(2R,3R)-2-(4,4-difluoro-3-oxooctyl)-5-oxo-3-(tetrahydropyranyloxy)cyclopentyl]nonanoate (91)

The compound (90) (0.301 g) was subjected to Swern oxidation using oxalyl chloride (0.34 ml), DMSO (0.61 ml) and triethylamine (1.22 ml) in dichloromethane to give the entitled compound (91). Yield: 0.288 g (96%).

8-4) Preparation of isopropyl 9-(1R)-[(2R,3R)-2-(4,4 difluoro-3-oxooctyl)-3-hydroxy-5-oxocyclopentyl] nonanoate (92)

The compound (91) (0.288 g) was dissolved in a mixed solvent (30 ml) consisting of acetic acid, water and THF (4:2:1) and the solution was kept at 45° C. for 3.5 hours. The resultant mixture was worked up with the conventional procedure and the obtained crude product was subjected to silicagel column chromatography to give the titled compound (92). Yield: 0.184 g (76%).

Compound (92) [$Q_1'=Q_2'=F$, $Rb'-Rc'=butyl$, $P_3=isopropyl$]

NMR(CDCl$_3$) δ: 0.94 (t,3H,J=6.5Hz), 1.24 (d,6H,J=6Hz), 1.27–2.95 (m,31H), 4.19 (m,1H), 5.02 (Hept,1H,J=6Hz)

The compounds of the formula I wherein D is —CO—CH$_2$— and those wherein D is —C≡C— can be prepared as follows:

PREPARATION EXAMPLE 9

Preparation of 2-decarboxy-2-(2-carboxyethyl)-13,14-dihydro-6,15-diketo-PGF$_{1\alpha}$ isopropyl ester The compound (75) obtained in Preparation Example 3 is dissolved in a mixture of anhydrous tetrahydrofuran and anhydrous methylenechloride. A small excess amount of N-bromosuccinimide is added to the Solution at 0° C. and the resultant mixture is stirred for 5 minutes. The resultant mixture is worked up with the conventional procedure and the crude product is subjected to column chromatography to give the compound (93) ($Q_1'=Q_2'=H$, $Rb'-Rc'=butyl$, $P_1=tetrahydroxypyranyl$, $P_2=ethylene$, $P_3=isopropyl$). This is dissolved in anhydrous toluene. The solution is treated with DBU and stirred overnight at 40° C. After cooling with ice, the solution is acidified with N-HCl, stirred for 10 minutes and extracted with ethyl acetate. The resultant mixture is worked up with the conventional procedure and the residue is subjected to column chromatography to give the compound (94) (symbols having the same meaning as above). Removal of the protective groups in a manner similar to that in the step 3-3) in Preparation Example 3 gives the titled compound.

PREPARATION EXAMPLE 10

Preparation of 2-decarboxy-2-(2-carboxyethyl)-5,6-dehydro-13,14-dihydro-15-keto-PGE$_2$ methyl ester Tert-butyl lithium is added dropwise to a solution of 8-methoxy-3,3-ethylenedioxy-1-iodooctane (prepared according to JP-A-52753/1989) in ether at −78° C. over 30 minutes and the resultant mixture is stirred for 3 hours. Then a solution, cooled to −78° C., of cuprous iodide and tributylphosphine in ether is added to the above mixture in one portion and the resultant mixture is stirred for 20 minutes to form the complex (j). A solution of 4R-tertbutyldimethylsililoxy-2-cyclopenten-1-one (95) in tetrahydrofuran is added dropwise to the mixture over 95 minutes. The resultant mixture is stirred for 15 minutes and transferred to a cooling bath at −30° C. A solution of 8-methoxycarbonyl-1-iodooctyne (κ) in HMPA is added to the cooled mixture, which is then stirred for 4.5 hours. Stirring is continued at the room temperature for 12 hours and then the mixture is poured into an aqueous ammonium chloride. The organic layer is separated and worked up with the conventional procedure to give a crude product. The crude product is subjected to column chromatography to give the compound (96) [Q$_1'$=Q$_2'$=H, Rb'—Rc'=butyl, P$_3$=methyl, P$_5$=tert-butyldimethyl]. Deprotection of this in the conventional manner gives the titled compound.

PREPARATION EXAMPLE 11

Preparation of 2-decarboxy-2-(2-carboxyethyl)-13,14-dihydro-16,16-difluoro-15-keto-PGF$_{2\alpha}$ methyl ester (72) [IUPAC nomenclature: methyl (Z)-9-(1R)-[(2R,3R,5S)-2-(4,4-difluoro-3-oxooctyl)-3,5-dihydroxycyclopentyl]-7-nonenoate

11-1) Preparation of (1S,5R,6R,7R)-6-[3(R,S)-t-butytdimethylsilyloxy-4,4-difluorooctyl]-7-(tetrahydropyranyloxy)-2-oxabicyclo[3.3.0]octan-3(R,S)-ol (98)

The compound (84) [Q$_1'$=Q$_2'$=F, P$_1$=tetrahydropyranyl, Rb'—Rc'=butyl](1.26 g) was treated with imidazole (2.63 g) and tert-butyldimethylsilyl chloride (2.91 g) in DMF (15 ml) to give the silyl ether (97). Yield: 1.43 g (88%).

The silyl ether (97) (1.43 g) was reduced with diisobutylalminum hydride in the conventional procedure to give the titled compound (98). Yield: 1.47 g (100%).

11-2) Preparation of methyl (Z)-9-(1R)-[(2R,3R,5S)-2-{3(R,S)-tert-butyldimethylsilyloxy-4,4-difluorooctyl}-5-hydroxy-3-(tetrahydropyranyloxy)cyclopentyl]-7-nonenoate (100)

A ylid was prepared from sodium hydride (60%, 0.934 g), DMSO (25 ml) and (6-carboxyhexyl)triphenylphosphonium bromide (5.50 g) in the conventional procedure. The ylid was added to a solution of the compound (98)in ether (8 ml) and the resultant mixture was stirred at the room temperature for 2 hours. The resultant mixture was worked with the conventional procedure to give the carboxylic acid (99), which was treated with diazomethane. The product was subjected to silicagel column chromatography to give the titled compound (100). Yield: 0.43 g (48%).

11-3) Preparation of methyl (Z)-9-(1R)-[(2R,3R,5S)-2-{3(R,S)-tert-butyldimethylsilyloxy-4,4,-difluorooctyl}-3,5-(ditetrahydropyranyloxy)cyclopentyl]-7-nonenoate (101)

The compound (100) (0.438 g) was converted to ditetrahydropyranyl ether using an excess amount of dihydropyran and a catalytic amount of p-toluenesulfonic acid in dichloromethane (25 ml). The resultant mixture was subjected to silicagel column chromatography to give the compound (101). Yield: 0.494 g (99%).

11-4) Preparation of methyl (Z)-9-(1R)-[(2R,3R,5S)-2-(tertbutyldimethylsilyloxy-3-oxooctyl)-3.5-(ditetrahydropyranyloxy)cyclopentyl]-7-nonenoate (103)

The compound (101) (0.494 g) was dissolved in THF (10 ml). Tetrabutylammonium trifluoride (1.0M, 5.6 ml) was added to the solution and the resultant mixture was kept overnight. Then the resultant mixture was worked up with the conventional procedure to give the deprotected compound (102). Yield: 0.284 g (68%).

The compound (102) (0.284 g) was subjected to Swern oxidation using oxalyl chloride (0.165 ml) and DMSO (0.3 ml) in dichloromethane (10 ml). The product was subjected to silicagel column chromatography to give the compound (103). Yield: 0.251 g (89%).

11-5) Preparation of methyl (Z-9-(1R)-[(2R,3R,5S)-2-(4,4-difluoro-3-oxooctyl)-3,5-dihydroxycyclopentyl]-7-nonenoate (104)

The compound (103) was dissolved in a mixed solvent (30 ml) consisting of acetic acid, water and THF (4:2:1) and the solution was kept at 45° to 50° C. for 3 hours. The resultant mixture was worked up with the conventional procedure and the obtained crude product was subjected to silicagel column chromatography to give the titled compound (104). Yield: 0.137 (76%).

Compound (72) [Q$_1'$=Q$_2'$=F, Rb'—Rc'=butyl, P$_3$=methyl]

NMR(CDCl$_3$) δ: 0.92 (t,3H,J=7.5Hz), 1.2–2.9 (m,38H), 3.67 (s,3H), 3.70 (q,1H,J=7.5Hz), 4.25 (m,1H), 5.43 (m,2H).

PREPARATION EXAMPLE 12

Preparation of 2-decarboxy-2-(2-carboxyethyl)-13,14-dihydro-16,16-difluoro-15-keto-PGE$_1$ (105) [IUPAC nomenclature: (Z)-9-(1R)-[(2R,3R,5S)-2-(4,4-difluoro-3-oxooctyl)-3-hydroxy-5-oxocyclopentyl]nonanoic acid]

12-1) Preparation of benzyl (Z)-9-(1R)-[(2R,3R,5S)-3-{4,4-difluoro-3(R,S)-hydroxyoctyl}-5-hydroxy-3-(tetrahydropyranyloxy)cyclopentyl]-7-nonenoate (87)

The compound (54) [Q$_1'$=Q$_2'$=F, P$_1$=tetrahydropyranyl, Rb'—Rc'=butyl](1.09 g) was dissolved in acetonitrile (20 ml) and DBU (2.6 ml) and benzyl bromide (2.2 ml) were added to the solution. The resultant mixture was kept at 45° C. for 1 hour and then overnight at 60° C. The resultant mixture was worked up with the conventional procedure and the obtained crude product was subjected to silicagel column chromatography to give the titled compound (87). Yield: 0.213 g.

12-2) Preparation of benzyl (Z)-9-(1R)-[(2R,3R,5S)-2-(4,4-difluoro-3-oxooctyl-3-tetrahydropyranyloxy)-5-oxocyclopentyl]-7-nonenoate (88)

The compound (87) (0.213 g) was subjected to Swern oxidation using oxalyl chloride (0.23 ml), DMSO (0.41 ml) and triethylamine (0.81 ml) in dichloromethane (15 ml). The product was subjected to silicagel column chromatography to give the titled compound (88). Yield: 0.181 g (86%).

12-3) Preparation of benzyl (Z)-9-(1R)-[(2R,3R,5S)-2-(4,4-difluoro-3-oxooctyl)-3-hydroxy-5-oxocyclopentyl]-7-nonenoate (78)

The compound (88) (0.181 g) was dissolved in a mixed solvent (25 ml) consisting of acetic acid, water and THF (4:2:1) and the solution was kept at 45° C. for 3.5 hours. The resultant mixture was worked up with the conventional procedure and the obtained crude product was subjected to silicagel column chromatography to give the titled compound (78). Yield: 0.140 g (91%).

Compound (78) [$Q_1'=Q_2'=F$, $Rb'-Rc'=butyl$, $P_3=benzyl$].

NMR(CDCl$_3$) δ: 0.93 (t,3H,J=7.5Hz), 1.2–2.8 (m,27H), 4 20 (m,1H), 5.12 (s,2H), 5.2–5.5 (m,2H), 7.35 (m,5H).

12-4) Preparation of 9-(1R)-[(2R,3R,5S)-2-(4,4-difluoro-3-oxooctyl-3-hydroxy-5-oxocyclopentyl]nonanoic acid (105)

The compound (78) was dissolved in ethyl acetate (15 ml). Palladium on carbon (50mg) was added to the solution and shaken under the hydrogen atmosphere. After removing the catalyst by filtration, the filtrate was concentrated and the produced crude product was subjected to Lobar column (ODS) chromatography to give the titled compound (105). Yield: 0.077 g (65%).

Compound (105) [$Q_1'=Q_2'=F$, $Rb'-Rc'=butyl$].

NMR(CDCl$_3$) δ: 0.95 (t,3H,J=7.5Hz), 1.2–2.8 (m,32H), 4.20(m,1H).

PREPARATION EXAMPLE 13

Preparation of 20-ethyl-2-decarboxy-2-(2-carboxyethyl)-13,14-dihydro-16,16-difluoro-15-keto-PGE$_1$ isopropyl ester (92) [IUPAC nomenclature: isopropyl (Z)-9-(1R)-[(2R, 3R)-2-(4,4-difluoro-3-oxodecyl)-3-hydroxy-5-oxocyclopentyl]- 7-nonenoate]

The procedure of Preparation Example 6 was repeated except that dimethyl (3,3-difluoro-2-oxononyl)-phosphonate was used to give the titled compound (60).

Compound (92) [$Q_1'=Q_2'=F$, $Rb'-Rc'=hexyl$, $P_3=isopropyl$]

NMR(CDCl$_3$) δ: 0.90 (t,3H,J=7.5Hz), 1.32 (d,6H,J=6Hz), 1.25–2.70 (m,34H), 3.15 (s,1H), 4.20 (m,1H), 5.00 (Hept,1H,J=7.5Hz).

PREPARATION EXAMPLE 14

Preparation of 2-decarboxy-2-(2-carboxyethyl)-13,14-dihydro-15-keto-PGE$_2$ isopropyl ester (78) [IUPAC nomenclature: isopropyl (Z)-9-(1R)-[(2R,3R)-2-(3-oxopentyl)-3-hydroxy-5-oxocyclopentyl]-7-nonenoate]

The procedure of Preparation Example 4 was repeated except that dimethyl 2-oxoheptylphosphonate was used to give the titled compound (78).

Compound (78) [$Q_1'=Q_2'=H$, $Rb'-Rc'=butyl$, $P_3=isopropyl$].

NMR(CDCl$_3$) δ: 0.89 (t,3H, J=6.6Hz ), 1.18 (d,6H,J=6.2Hz), 1.15–3.0 (m,29H), 4.04 (m,1H), 4.99 (hept,1H, J=6.2Hz), 5.37 (m,2H).

FORMULATION EXAMPLE 1

Powders for Injection

|  | (Parts by weight) |
|---|---|
| 3,14-dihydro-15-keto-16,16-difluoro-PGE$_2$ | 1 |
| mannitol | 5 |
| distilled water | 0.4 |

The above ingredients were mixed, stirred, sterilized, filtered and lyophilized to give powders for injection.

FORMULATION EXAMPLE 2

Injectable Solution

|  | (Parts by weight) |
|---|---|
| 13,14-dihydro-15-keto-16,16-dimethyl-PGE$_2$ | 0.2 |
| nonion surfactant | 2 |
| distilled water | 98 |

The above ingredients were mixed and sterilized to give an injectable solution.

FORMULATION EXAMPLE 3

13,14-dihydro-15-keto-16,16-difluoro-20-ethyl-PGE$_2$ (50 mg) dissolved in methanol (10 ml) was mixed with mannitol (18.5 g). The mixture was screened (with a sieve, the pore size of which being 30 mm in diameter), dried and screened again. The powders thus obtained were mixed with fine-grain silica gel (Aerosil*, 200 g) and filled in No. 3 hard gelatin capsules (100) to give enteric capsules which contain 0.5 mg of 13,14-dihydro-15-keto-16,16-difluoro-20-ethyl-PGE$_2$ per capsule.

FORMULATION EXAMPLE 4

Powders for Oral Administration

|  | (Parts by weight) |
|---|---|
| 13,14 dihydro-15-keto-16,16-difluoro-PGF$_{2\alpha}$ methyl ester | 5 |
| light anhydrous silicic acid | 5 |
| Abicel* | 20 |
| lactose | 70 |

*Trade Mark

The above ingredients were mixed to give powders for oral administration.

FORMULATION EXAMPLE 5

Soft Gelatine Capsules

|  | (Parts by weight) |
|---|---|
| 13,14-dihydro-15-keto-16,16-difluoro-20-methyl-PGE$_2$ methyl ester | 1 |
| Panasate* | 20 |

*Trade Mark

The above ingredients were mixed and filled in soft gelatine capsules.

FORMULATION EXAMPLE 6

Enteric Capsules 16-desbutyl-13,14-dihydro-15-keto-16-(m-trifluoromethyl)phenoxy-PGF$_{2\alpha}$ methyl ester (50 mg) dissolved in methanol (10 ml) was mixed with mannitol (18.5 g). The mixture was screened (with a sieve, the pore size of which being 30 mm in diameter), dried for 90 minutes at 30° C. and screened again. The powders thus obtained were mixed with fine-grain silica gel (Aerosil*, 200 g) and filled in No. 3 hard gelatin capsules (100) to give enteric capsules which contain 0.5 mg of 13,14-dihydro-15-keto-16-desbutyl-16-m-trifluoromethylphenoxy-PGF$_{2\alpha}$ methyl ester per capsule.

FORMULATION EXAMPLE 7

Powders for Injection

|  | (Parts by weight) |
|---|---|
| 13,14-dihydro-15-keto-16-desbutyl-16-m-trifluoromethylphenoxy-PGF$_{2\alpha}$ methyl ester | 1 |
| mannit | 5 |
| distilled water | 0.4 |

The above ingredients were mixed and sterilized to give and injectable solution.

FORMULATION EXAMPLE 8

Injectable Solution

|  | (Parts by weight) |
|---|---|
| 13,14-dihydro-6,15-diketo-5R,S-fluoro-PGE$_1$ | 0.2 |
| nonion surfactant | 2 |
| distilled water | 98 |

The above ingredients were mixed and sterilized to give and injectable solution.

FORMULATION EXAMPLE 9

Powders for Oral Administration

|  | (Parts by weight) |
|---|---|
| 13,14-dihydro-15-keto-16-desbutyl-16-m-trifluoromethylphenoxy-PGE$_2$ methyl ester | 5 |
| light anhydrous silicic acid | 5 |
| Abicel* | 20 |
| lactose | 70 |

*Trade Mark

The above ingredients were mixed to give powders for oral administration.

FORMULATION EXAMPLE 10

Soft Gelatine Capsules

|  | (Parts by weight) |
|---|---|
| 13,14-dihydro-15-keto-16-desbutyl-16-m-trifluoromethylphenoxy-PGE$_2$ methyl ester | 1 |
| Panasate* | 899 |

*Trade Mark

The above ingredients were mixed and filled in soft gelatine capsules.

FORMULATION EXAMPLE 11

Eye Drop

|  |  |
|---|---|
| 13,14-dihydro-15-keto-20-ethyl-PGF$_{2\alpha}$ isopropyl ester | 10 mg |
| Physiological saline | 10ml |

The above ingredients were placed in separate vials and combined for mixing on use to form an eye drop.

In the above formulation examples, the active ingredient can be replaced by any other compound within the compounds used in the invention.

TEST EXAMPLE 1

Method

Male Wistar rats (weight: about 120 g) were used as the test animals. The animals were allotted to groups, each consisting of 10 animals (20 eyes). Fifteen minutes after the administration of a test compound, 0.05 ml of 1% carrageenan in physiological saline was injected subconjunctivally at an upper eyelid of the animals through a microsyringe to induce an edema. After 4 hours, the animals were sacrificed by vertebral cervial dislocation. Parts of conjunctive showing inflammation was cut off and separately weighed. The test compound was dissolved in the physiological saline and administered ocularly (5µl/eye). The control received the physiological saline.

Results

The results are shown in Table 1.

TABLE 1

| Test Compound | Dose (µg/eye) | Weight of Conjunctive (Mean ± S.D.) |
|---|---|---|
| (control) | 0 | 66.7 ± 11.8 |
| 1 | 6 | 56.3 ± 15.3* | t-Test
*P < 0.01
Test compound 1: 13,14-dihydro-15-keto-20-ethyl-PFG$_{2\alpha}$ isopropyl ester

TEST EXAMPLE 2

The procedure of Test Example 1 was repeated except that 13,14-dihydro-15-keto-16,16-difluoro-PGE$_2$ (Test Compound 2) was used as the test compound. In addition, results after subcutaneous administration (5 ml/kg) were observed. The results are shown in Tables 2 and 3.

TABLE 2

| | (ocular administration) | |
|---|---|---|
| Test Compound | Dose (µg/eye) | Weight of Conjunctive (Mean ± S.D.) |
| (control) | 0 | 67.7 ± 2.1 |

TABLE 2-continued (ocular administration)

| Test Compound | Dose (μg/eye) | Weight of Conjunctive (Mean ± S.D.) |
|---|---|---|
| 2 | 1 | 54.3 ± 3.7** |

TABLE 3

(subcutaneous administration)

| Test Compound | Dose (μg/eye) | Weight of Conjunctive (Mean ± S.D.) |
|---|---|---|
| (control) | 0 | 67.7 ± 2.1 |
| 2 | 10 | 59.9 ± 2.5 |

DUNNET Test
**P < 0.01

TEST EXAMPLE 3

Method

Male Wistar rats (weight: about 120 g) were used as the test animals. The animals were allotted to groups, each consisting of 10 animals (20 eyes). Two minutes after the administration of test compounds, 0.5% Evans Blue in physiological saline (0.5 ml) was injected in the caudal vein to elicit the PCA reaction. Immediately after, 0.1% histamine hydrochloride in physiological saline (50 μl) was injected subconjunctivally at an upper eyelid. After 30 minutes, the animals were sacrificed by vertebral cervial dislocation and the scalp was peeled away towards the eyelid. Part of skin and conjunctive showing inflammation was cut off and weighed. Then, said conjunctive was minced and extracted overnight with 4 ml formaldehyde at 40° C. with shaking. The dye in the conjunctive was assayed by measuring absorption of the extract at 625 nm. The test compounds were dissolved in the physiological saline and administered ocularly (5 μl/eye). The control received the physiological saline.

Results

The results are shown in Table 4.
Table 4

TABLE 4

| Test Compound | Dose (μg/eye) | Weight of Conjunctive (Mean ± S.D.) | Dye (μg/part) |
|---|---|---|---|
| (control) | 0 | 42.9 ± 3.1 | 11.25 ± 0.89 |
| 2 | 3 | 38.0 ± 2.0 | 7.08 ± 0.87** |
| 3 | 3 | 39.0 ± 2.2 | 7.95 ± 0.59 |

DUNNET Test
**P < 0.01
Test Compounds
2: See Test Example 2
3: 13,14-dihydro-15-keto-16,16-difluoro-PGE$_2$ methyl ester

TEST EXAMPLE 4

The procedure of Test Example 3 was repeated except that Test Compound 1 (see: Test Example 1) as the test compound and 10 μl of 0.1% histamine hydrochloride in physiological saline were used. The results are shown in

TABLE 5

| Test Compound | Dose (μg/eye) | Weight of Conjunctive (Mean ± S.D.) | Dye (μg/part) |
|---|---|---|---|
| (control) | 0 | 38.2 ± 1.8 | 5.59 ± 0.36 |
| 1 | 6 | 30.1 ± 2.1** | 3.95 ± 0.41*** |

DUNNET Test
**P < 0.01
***P < 0.05

From the above results, it can be clearly seen that the test compounds have an activity inhibiting experimental conjunctivitis.

In the following data, NMR spectra were measured in CDCl$_3$ using HITACHI R-90H and mass spectra were measured by EI method at an ionization potential of 70eV using HITACHI M-80B.

* 13,14-dihydro-15-keto-16,16-difluoro-PGE$_2$. $^1$H NMR (CDCl$_3$) δ0.93(t,3H,J=7.5 Hz), 1.20–2.70(m,2H), 4.20 (m,1H), 5.40(m,2H).
MS (DI-EI) m/z 388(M$^+$), 370(M$^+$—H$_2$O), 352(M$^+$—2H$_2$O).

* 13,14-dihydro-15-keto-16,16-difluoro-PGE$_1$ isopropyl ester.
$^1$H NMR (CDCl$_3$) δ0.93(t,3H,J=7.5 Hz), 1.23(d,J=7.5 Hz), 1.20–2.70(m,26H), 3.15(s,1H), 4.18(m,1H), 5.00(ht,1H,J=7.5 Hz).
MS (DI-EI) m/z 432(M$^+$), 414(M$^+$—H$_2$O).

* 13,14-dihydro-15-keto-16,16-difluoro-PGE$_2$ isopropyl ester.
$^1$H NMR (CDCl$_3$) δ 0.93(t,3H,J=7.5 Hz), 1.23(d,6H,J=7.5 Hz), 1.30–2.70(m,22H), 2.78(s,1H), 4.20(m,1H), 5.00(ht,1H,J=7.5 Hz).
MS (DI-EI) m/z 430(M$^+$), 412(M$^+$—H$_2$O).

* 13,14-dihydro-15-keto-16,16-difluoro-19-desmethyl-PGE$_2$ methyl ester.
$^1$H NMR (CDCl$_3$) δ 0.98(t,3H,J=7.5 Hz), 1.50–2.70(m,20H), 2.94 (s,1H), 3.68(s,3H), 4.20(m,1H), 5.40(m,2H).
MS (DI-EI) m/z 388(M$^+$), 370(M$^+$—H$_2$O), 357(M$^+$—H$_2$O—CH$_3$O), 355(M$^+$—H$_2$O—CH$_3$).

* 13,14-dihydro-15-keto-16,16-difluoro-19-desmethyl-PGE$_2$.
$^1$H NMR (CDCl$_3$) δ 0.98(t,3H,J=7.5 Hz), 1.40–2.70(m,22H), 4.20 (m,1H), 5.40(m,2H).
MS (DI-EI) m/z 374(M$^+$),356(M$^+$—H$_2$O), 338(M$^+$—2H$_2$O).

13,14-dihydro-15-keto-16,16-difluoro-11-dehydroxy-11-methyl-PGE$_2$ methyl ester.
$^1$H NMR (CDCl$_3$) δ 0.93(t,3H,J=7.5 Hz), 1.14(d,3H,J=6 Hz), 1.25–2.80(m,22H), 3.63(s,3H), 5.38(m,2H).
MS (DI-EI) m/z 400(M$^+$), 369(M$^+$—CH$_3$O).

13,14-dihydro-15-keto-16,16-difluoro-PGD$_2$ methyl ester
$^1$H NMR (CDCl$_3$) δ 0.91(t,3H,J=7.5 Hz), 1.20–3.20(m,23H), 3.68 (s,3H), 4.44(m,1H,J=1.2 Hz), 5.49(m,2H).
MS (DI-EI) m/z 402(M$^+$), 384(M$^+$—H$_2$O), 353(M$^+$—H$_2$O—CH$_3$O).

* 13,14-dihydro-15-keto-16,16-difluoro-20-methyl-PGE$_2$.
$^1$H NMR (CDCl$_3$) δ 0.90(t,3H,J=7.5 Hz), 1.20–2.70(m,26H), 4.20 (m,1H), 5.41(m,2H).
MS (DI-EI) m/z 402(M$^+$), 384(M$^+$—H$_2$O), 366(M$^+$—2H$_2$O)

* 13,14-dihydro-15-keto-16,16-difluoro-20-ethyl-PGE$_2$ methyl ester.

$^1$H NMR (CDCl$_3$) δ 0.89(t,3H,J=7.5 Hz), 1.20–2.70(m,26H), 2.93 (s,1H), 3.68(s,3H), 4.20(m,1H), 5.41(m,2H).

MS (DI-EI) m/z 430(M+), 412(M+—H$_2$O), 399(M+—CH$_3$O), 381(M+—H$_2$O—CH$_3$O).

\* 13,14-dihydro-15-keto-16,16-difluoro-20-ethyl-PGE$_2$ $^1$H NMR (CDCl$_3$) δ 0.94(t,3H,J=7.5 Hz), 1.20–2.70(m,27H), 4.21 (m,1H), 5.43(m,2H).

MS (DI-EI) m/z 416(M+), 398(M+—H$_2$O), 380(M+—2H$_2$O).

What is claimed is:

1. A method of treatment of a patient having an inflammation characterized by lesions caused by a defensive reaction or an inflammatory reaction of the patient and having signs of redness, heat, pain, swelling and loss of function which comprises administering, to a subject in need of such treatment, an anti-inflammatorily effective amount of a 15-keto-prostaglandin compound having the formula:

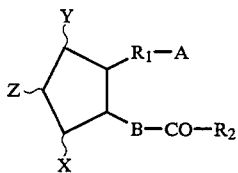

wherein X and Y are hydrogen, hydroxy, halo, lower alkyl, hydroxy(lower)alkyl, or oxo, with the proviso that at least one of X and Y is a group other than hydrogen, and the 5-membered ring may have at least one double bond, Z is hydrogen or halo, A is —CH$_2$OH, —COCH$_2$OH, —COOH or its functional derivative, B is —CH$_2$—CH$_2$, —CH=CH— or —C≡C—, R$_1$ is a bivalent saturated or unsaturated, lower or medium aliphatic hydrocarbon residue which is unsubstituted or substituted with halo, oxo or aryl, R$_2$ is a saturated or unsaturated, lower or medium aliphatic hydrocarbon residue which is unsubstituted or substituted with halo, hydroxy, oxo, lower alkoxy, lower alkanoyloxy, cyclo(lower)alkyl, aryl or aryloxy, and a carbon atom of R$_2$ adjacent to the "CO" is substituted by at least one halogen atom; or R$_2$ is a saturated or unsaturated aliphatic hydrocarbon residue containing a 5 carbon atom chain attached to the "C" of the "CO" which is unsbustituted or substituted with halo, hydroxy, oxo, lower alkoxy, lower alkanoyloxy, cyclo(lower)alkyl, aryl or aryloxy, [and said carbon atom of R$_2$ adjacent to the CO is substituted by at least one halogen atom or ] and the terminal carbon atom of R$_2$ is substituted by a lower alkyl.

2. The method according to claim 1, wherein said 15-keto-prostaglandin compound is a 16-mono- or di-halo-15-keto-prostaglandin compound.

3. The method according to claim 1, wherein said 15-keto-prostaglandin compound is a 13,14-dihydro-16-mono- or di-halo-15-keto-prostaglandin compound.

4. The method according to claim 1, wherein said 15-keto-prostaglandin compound is a 13,14-dihydro-16-mono- or di-fluoro-15-keto-prostaglandin compound.

5. The method according to claim 1, wherein said 15-keto-prostaglandin compound is a 13,14-dihydro-6,15-diketo-prostaglandin compound.

6. The method according to claim 1, wherein said 15-keto-prostaglandin compound is a 15-keto-20-alkyl-prostaglandin compound.

7. The method according to claim 1, wherein said 15-keto-prostaglandin compound is a 13,14-dihydro-15-keto-20-alkyl-prostaglandin compound.

8. The method according to claim 1, wherein said 15-keto-prostaglandin compound is a 13,14-dihydro-15-keto-20-ethyl-prostaglandin compound.

9. The method according to claim 1, wherein said inflammation to be treated is conjunctivitis.

10. The method according to claim 1, wherein said compound is 13, 14-dihydro-15-keto-16, 16-difluoro-PGE or its lower alkyl ester.

11. The method according to claim 1, wherein said compound is 13, 14-dihydro-15-keto-20-ethyl-PGF or its lower alkyl ester.

12. The method according to claim 1, wherein said inflammation affects the eye.

\* \* \* \* \*